US010463452B2

(12) United States Patent
Matov et al.

(10) Patent No.: US 10,463,452 B2
(45) Date of Patent: Nov. 5, 2019

(54) METHOD TO VISUALIZE AND MANUFACTURE ALIGNER BY MODIFYING TOOTH POSITION

(71) Applicant: Align Technology, Inc., San Jose, CA (US)

(72) Inventors: Vadim Matov, San Jose, CA (US);
Fuming Wu, Pleasanton, CA (US);
Jihua Cheng, San Jose, CA (US);
Jennifer Chen, Alhambra, CA (US);
Chunhua Li, Cupertino, CA (US);
Bastien Pesenti, San Jose, CA (US);
Igor Kvasov, Santa Clara, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 15/684,775

(22) Filed: Aug. 23, 2017

(65) Prior Publication Data
US 2018/0055600 A1 Mar. 1, 2018

Related U.S. Application Data

(60) Provisional application No. 62/379,199, filed on Aug. 24, 2016.

(51) Int. Cl.
*A61C 7/00* (2006.01)
*A61C 7/08* (2006.01)
*G06F 17/50* (2006.01)

(52) U.S. Cl.
CPC ............... *A61C 7/002* (2013.01); *A61C 7/08* (2013.01); *G06F 17/50* (2013.01)

(58) Field of Classification Search
CPC ............................. A61C 7/0002; A61C 7/002
See application file for complete search history.

(56) References Cited

U.S. PATENT DOCUMENTS 2,467,432 A 4/1949 Kesling
3,407,500 A 10/1968 Kesling
(Continued)

FOREIGN PATENT DOCUMENTS

AU 3031677 A 5/1979
AU 517102 B2 7/1981
(Continued)

OTHER PUBLICATIONS

AADR. American Association for Dental Research, Summary of Activities, Mar. 20-23, 1980, Los Angeles, CA, p. 195.
(Continued)

*Primary Examiner* — Ralph A Lewis
(74) *Attorney, Agent, or Firm* — Wilson Sonsini Goodrich & Rosati

(57) ABSTRACT

Orthodontic systems and related methods are disclosed for designing and providing improved or more effective tooth moving systems for eliciting a desired tooth movement and/or repositioning teeth into a desired arrangement. Methods and orthodontic systems include the generation of an overcorrection in the tooth-receiving cavities of an appliance worn in the dentition. The overcorrection may provide an improved and more accurately applied force or moment applied to a tooth. The overcorrected force or moment can move a tooth closer to a desired position than if not overcorrected as sufficient force can still applied to the tooth as it gets closer to the desired position. The overcorrected force or moment may also better target the root of the tooth where the biological response to tooth movement occurs. The overcorrection may be calculated in various ways as described herein.

24 Claims, 12 Drawing Sheets

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,482,298 B1 | 11/2002 | Bhatnagar |
| 6,524,101 B1 | 2/2003 | Phan et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 7,320,592 B2 * | 1/2008 | Chishti .............. A61C 7/00 433/24 |
| 2002/0006597 A1 | 1/2002 | Andreiko et al. |
| 2003/0009252 A1 | 1/2003 | Pavlovskaia et al. |
| 2003/0139834 A1 | 7/2003 | Nikolskiy et al. |

(56) References Cited

U.S. PATENT DOCUMENTS

| | | |
|---|---|---|
| 2003/0224311 A1 | 12/2003 | Cronauer |
| 2004/0128010 A1 | 7/2004 | Pavlovskaia et al. |
| 2005/0055118 A1 | 3/2005 | Nikolskiy et al. |
| 2013/0230818 A1* | 9/2013 | Matov ............... A61C 7/00 433/3 |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| KR | 20020072318 A | 9/2002 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-2010059988 A1 | 5/2010 |
| WO | WO-2016135549 A1 | 9/2016 |
| WO | WO-2018039383 A1 | 3/2018 |

OTHER PUBLICATIONS

Alcaniz, et al., "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.
Alexander et al., "The DigiGraph Work Station Part 2 Clinical Management," JCO, pp. 402-407 (Jul. 1990).
Altschuler, "3D Mapping of Maxillo-Facial Prosthesis," AADR Abstract #607, 2 pages total, (1980).
Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging Applications for Automated Industrial Inspection and Assembly, vol. 182, p. 187-191 (1979).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "Integrated Three-Dimensional Craniofacial Mapping: Background, Principles, and Perspectives," Semin. in Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff, "Computerized Diagnostic Setups and Simulations," Angle Orthod., 40(1):28-36 (Jan. 1970).
Biggerstaff et al., "Computerized Analysis of Occlusion in the Postcanine Dentition," Am. J. Orthod., 61(3): 245-254 (Mar. 1972).
Biostar Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004.
Bourke, "Coordinate System Transformation," (Jun. 1996), p. 1, retrieved from the Internet Nov. 5, 2004, URL< http://astronomy.swin.edu.au/—pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form in Predetermination, Am, Journal of Orthodontics, vol. 79, No. 2 (Feb. 1981), pp. 115-133.
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Cardinal Industrial Finishes, Powder Coatings information posted at<http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Co-pending U.S. Appl. No. 15/051,364, filed Feb. 23, 2016.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside, Part 2 F. Duret—A Man with a Vision, Part 3 The Computer Gives New Vision—Literally, Part 4 Bytes 'N

(56) References Cited

OTHER PUBLICATIONS

Bites—The Computer Moves from the Front Desk to the Operatory," Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004<http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim. htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet:<http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).

Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstresspu-tonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).

(56) References Cited

OTHER PUBLICATIONS

McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventors CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances,< http:// www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art'?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording The Dental Cast in Three Dimensions," Am. J. Orthod. Dentofacial Orthop., 92(3):199-206 (Sep. 1987).

Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients,< http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050342, filed Jun. 20,1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.

(56) References Cited

OTHER PUBLICATIONS

Williams, "Dentistry and CAD/CAM: Another French Revolution," J. Dent. Practice Admin., pp. 2-5 (Jan./Mar. 1987).

Williams, "The Switzerland and Minnesota Developments in CAD/CAM," J. Dent. Practice Admin., pp. 50-55 (Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).

Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).

You May Be a Candidate for This Invisible No-Braces Treatment, Allesee Orthodontic Appliances-Pro Lab product information for patients, 2 pages (2002).

International search report with written opinion dated Dec. 5, 2017 for PCT/US2017/048275.

* cited by examiner

METHOD TO VISUALIZE AND MANUFACTURE ALIGNER BY MODIFYING TOOTH POSITION

CROSS-REFERENCE

This application claims the benefit of U.S. Provisional Application No. 62/379,199, filed Aug. 24, 2016, which application is incorporated herein by reference.

BACKGROUND OF THE INVENTION

Prior methods and apparatus for aligning teeth can be less than ideal in at least some instances. While braces can be used to move teeth into alignment, braces can be cumbersome to wear and can require expertise to place on the subject. Also, complex movements can be difficult to achieve and orthodontic placement may less than ideally address the complex movements of several teeth in at least some instances.

Transparent shell appliances have been used to successfully move teeth. For example a user can be provided with a series of transparent shell appliances. Each shell of the series of shells may correspond to a stage of the treatment. For example, a fourth shell in a series of ten shells may correspond to the fourth state of treatment. Although transparent shell appliances can be used to successfully reposition teeth, the transparent shell appliances can provide less than ideal results in at least some instances. For example, complex movements of teeth, such as to fill an extraction can be difficult to treat with transparent shell appliances. Also, in at least some instances, a wearer of a transparent shell appliance may not complete treatment, for example when teeth do not move sufficiently with the appliance and the user stops treatment. Additionally, in at least some instances, the course of treatment may need to be reevaluated as the treatment is implemented, which may necessitate the manufacture of a second series of transparent shell appliances, prolonging treatment time.

Prior methods and apparatus of aligning teeth with transparent shell appliances can rely on providing shells with cavities shaped to the tooth profile at a final intended position and orientation at a stage of the treatment. Work in relation to embodiments suggests cavities shaped to position a tooth at a final intended position and orientation at a stage of the treatment can provide less than ideal movement. Although attachments can be placed on teeth to facilitate movement of the teeth with polymeric shell appliances, the resulting movements can be less than ideal in at least some instances. For example, the force applied to the tooth can decrease as the tooth moves toward the target position. Also, the movement of a tooth may not be uniform, and the tooth may move more easily along some dimensions than others. For example, the movement of a tooth can occur along six degrees of freedom, and relative movement compared to a target movement can differ among the degrees of freedom of the tooth. Further, the movement of teeth can be coupled, such that movement of a first tooth can affect movement adjacent teeth.

Prior appliances to move teeth may provide teeth receiving cavities at locations corresponding to the locations of the teeth at the end of each stage of treatment. This approach can be less than ideal in at least some instances.

Although manufacturing appliances in accordance with target positions of the teeth at the end of each stage of treatment can be effective, work in relation to embodiments suggests that the amount of force applied to each tooth can be less than or greater than would be ideal, and the corresponding movement of the tooth can be less than ideal in at least some instances. There can be a discrepancy between the locations of the teeth receiving cavities of the polymeric shell appliance applied and current positions of the teeth. The force and moment may be created from the deformation of the polymeric shell appliance put on the teeth. When a tooth is moved close to its position in the next stage of the treatment course, the discrepancy between the polymeric shell appliance used and the tooth also can get smaller. Accordingly, the force applied by the polymeric shell appliance can be also reduced. When the force is small enough, there may be no tooth movement achieved until the next polymeric shell appliance with a new, larger discrepancy is used. Additionally, the force and moment created by the polymeric shell appliance can be from the discrepancy of the crown part of the tooth, and may be applied on tooth crown only, for example. However, the biological response for tooth movement can be generally centered on the tooth root and not the crown. Therefore, the force from the crown discrepancy may be less than ideal for root movement.

In light of the above, it would be desirable to provide improved methods and apparatus for moving teeth to target positions with polymeric shell appliances. Ideally such methods and apparatus would more accurately move teeth to target positions with decreased forces. In some embodiments, the methods, systems, and apparatus would allow dental practitioners to view, modify and approve suggested target tooth positions.

SUMMARY

Described herein are embodiments of systems and methods to generate modified, overcorrected positions for a set of appliances such as polymeric shell appliances. An "achievement matrix" may be generated by data analysis of past treated cases to generate the modified, overcorrected positions. Alternatively or in combination, a "force moment matrix" may be generated by measuring the force and moment from the discrepancy of a particular polymeric shell appliance from the teeth of a subject. Alternatively or in combination, a rotational component may be added to the pure translation movement of a particular polymeric shell appliance to compensate for the tipping effect while moving teeth.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference. U.S. Provisional Application No. 62/119,724, filed Feb. 23, 2015, U.S. Provisional Application No. 62/119,759, filed Feb. 23, 2015, and U.S. patent application Ser. No. 15/051,364, filed Feb. 23, 2016, are incorporated by reference herein in their entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
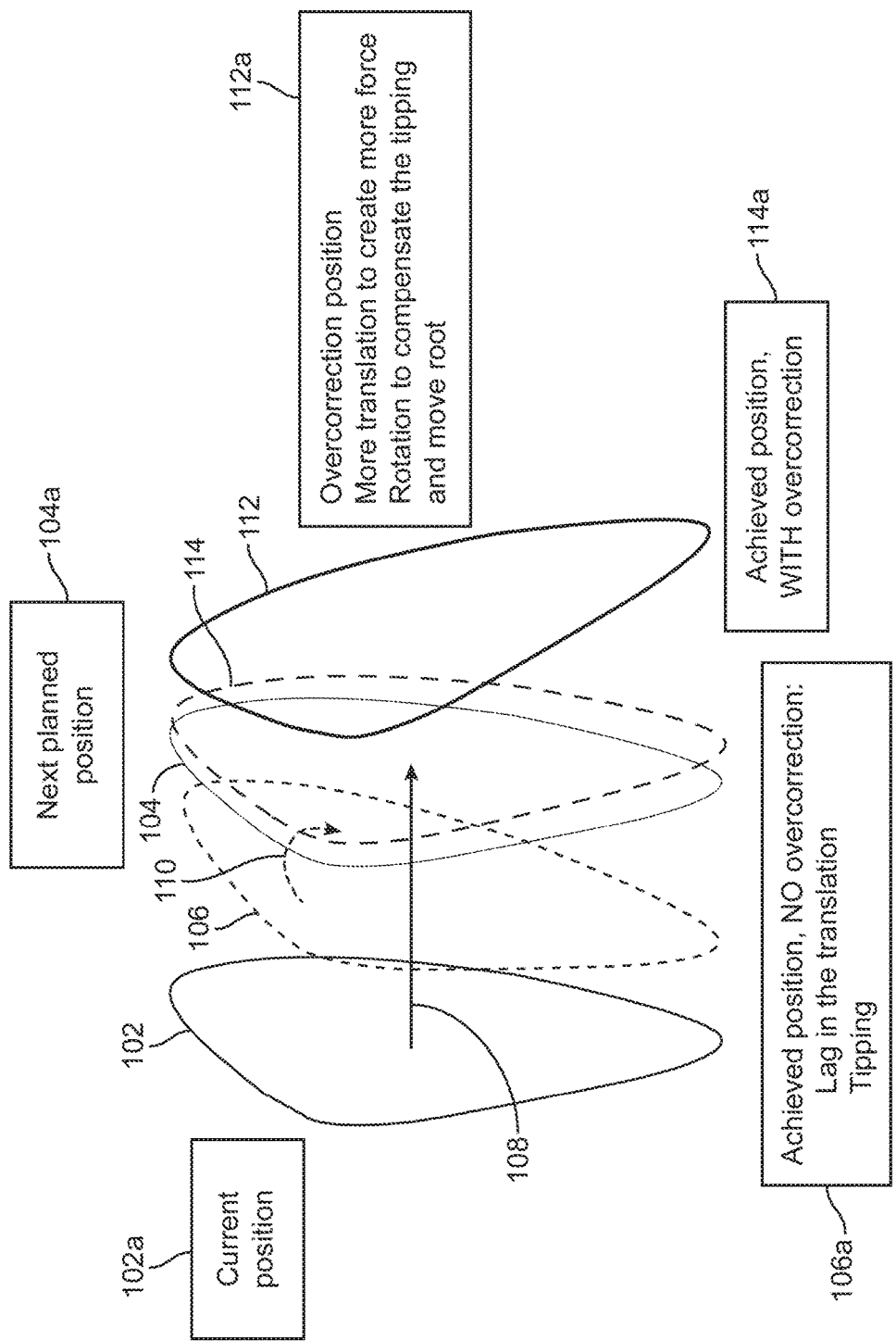
FIG. 1 shows a schematic of a tooth in a current position, a desired target position, an actual resulting position from the application of a plain polymeric shell appliance, an overcorrected position, and an actual resulting position from the application of a polymeric shell appliance of the present disclosure, according to many embodiments.

The present disclosure provides systems and methods to generate modified, overcorrected positions for a set of appliances such as polymeric shell appliances.

In one aspect, a system for moving one or more teeth with a dental appliance is provided. The system comprises a database comprising data corresponding to one or more of: (1) a plurality of discrepancies between target positions of teeth and achieved positions of the teeth in response to treatment, (2) a plurality of correlations between teeth movements and force systems applied by dental appliances, or (3) a plurality of clinical results of achieved teeth movements in response to force systems applied by dental appliances. The system can comprise a processing unit coupled to the database, wherein the processing unit is configured to determine an initial position of each of the one or more teeth, determine a target position for each of the one or more teeth in a treatment plan, and determine a movement vector to move said each of the one or more teeth from the initial position to the target position with an overcorrected tooth receiving cavity position determined in response to the data in the database.

In many embodiments, the database comprises one or more of patient treatment histories, orthodontic therapies, orthodontic information, or diagnostics.

In many embodiments, the data corresponds to the plurality of discrepancies, the plurality of discrepancies comprising a discrepancy of one or more of a force system, an achievement matrix, or clinical knowledge.

In many embodiments, the processing unit is configured to modify one or more tooth receiving cavity geometries of the dental appliance based on the overcorrected position.

In many embodiments, the movement vector is configured to establish a force system applied by the dental appliance to each tooth to move the tooth from the initial position to the target position with the overcorrected tooth receiving cavity position. The force system, when applied by the dental appliance, can move the tooth from the initial position to a position closer to the target position than the overcorrected tooth receiving cavity position. The force system can comprise one or more of a force, a moment of a force, or a moment of a couple.

In many embodiments, the movement vector is further determined in response to one or more of a minimum or maximum vertex distance.

In many embodiments, the processing unit is further configured to determine an overcorrected tooth receiving cavity corresponding to the overcorrected tooth receiving cavity position, the overcorrected tooth receiving cavity comprising a three dimensional shape profile to receive a corresponding tooth having a corresponding three dimensional shape profile, the three dimensional shape profile of the tooth receiving cavity being one or more of rotated or translated relative to the corresponding three dimensional shape profile of the corresponding tooth in the target position in order to define the overcorrected tooth receiving cavity position.

In many embodiments, the dental appliance comprises a polymeric shell appliance.

In many embodiments, the processing unit is further configured to generate instructions for fabricating a dental appliance in accordance with any of the embodiments herein, wherein the dental appliance comprises a tooth receiving cavity having the overcorrected tooth receiving cavity position. The dental appliance, when positioned on the one or more teeth, can be shaped to move the one or more teeth from the initial position toward the target position along the movement vector.

In another aspect, a method for determining one or more tooth receiving cavity positions of a dental appliance for moving one or more teeth is provided. The method can comprise: providing a database comprising data corresponding to one or more of: (1) a plurality of discrepancies between target positions of teeth and achieved positions of teeth in response to treatments, (2) a plurality of correlations between teeth movements and force systems applied by dental appliances, or (3) a plurality of clinical results of achieved teeth movements in response to force systems applied by dental appliances; determining an initial position of the one or more teeth; determining a target position of each of the one or more teeth in a treatment plan; and determining an overcorrected position of one or more tooth receiving cavities of the dental appliance in response to the data in the database.

In many embodiments, the database comprises one or more of patient treatment histories, orthodontic therapies, orthodontic information, or diagnostics.

In many embodiments, the data corresponds to the plurality of discrepancies, the plurality of discrepancies comprising a discrepancy of one or more of a force system, an achievement matrix, or clinical knowledge.

In many embodiments, the method further comprises modifying a geometry of the one or more tooth receiving cavities of the dental appliance based on the overcorrected position.

In many embodiments, the dental appliance is configured to apply a force system to the tooth to move the tooth from the initial position to the target position with the overcorrected tooth receiving cavity position. The force system, when applied by the dental appliance, can move the tooth from the initial position to a position closer to the target position than the overcorrected position. The force system can comprise one or more of a force, a moment of a force, or a moment of a couple.

In many embodiments, determining the overcorrected position comprises limiting the overcorrected position in response to one or more of a minimum or maximum vertex distance.

In many embodiments, the method further comprises determining an overcorrected tooth receiving cavity corresponding to the overcorrected tooth receiving cavity position, the overcorrected tooth receiving cavity comprising a three dimensional shape profile to receive a corresponding tooth having a corresponding three dimensional shape profile, the three dimensional shape profile of the tooth receiving cavity being one or more of rotated or translated relative to the corresponding three dimensional shape profile of the corresponding tooth in the target position in order to define the overcorrected position.

In many embodiments, the dental appliance comprises a polymeric shell appliance.

In many embodiments, the method further comprises generating instructions for fabricating a dental appliance in accordance with any of the embodiments herein, wherein the dental appliance comprises a tooth receiving cavity having the overcorrected tooth receiving cavity position. The dental appliance, when positioned on the one or more teeth, can be shaped to move the one or more teeth from the initial position toward the target position along the movement vector. The method can further comprise fabricating the dental appliance.

In another aspect, a system for moving one or more teeth with a dental appliance is provided. The system can comprise a database comprising data corresponding to a plurality of discrepancies between target positions of teeth and achieved positions of the teeth in response to treatment, and a processing unit coupled to the database. The processing unit can be configured to determine one or more initial positions of the one or more teeth, determine a target position for each of the one or more teeth in a treatment plan, and determine a movement vector to move said each of the one or more teeth from the initial position to the target position with an overcorrected tooth receiving cavity position determined in response to the plurality of discrepancies.

In many embodiments, the database comprises one or more of patient treatment histories, orthodontic therapies, orthodontic information, or diagnostics.

In many embodiments, the plurality of discrepancies comprises a discrepancy of one or more of a force system, an achievement matrix, or clinical knowledge.

In many embodiments, the processing unit is configured to modify one or more tooth receiving cavity geometries of the dental appliance based on the overcorrected position.

In many embodiments, the movement vector is configured to establish a force system applied by the dental appliance to the tooth to move the tooth from the initial position to the target position with the overcorrected tooth receiving cavity position. The force system, when applied by the dental appliance, may move the tooth from the initial position to a position closer to the target position than the overcorrected tooth receiving cavity position. The force system can comprise one or more of a force, a moment of a force, or a moment of a couple.

In many embodiments, the movement vector is further determined in response to one or more of a minimum or maximum vertex distance.

In many embodiments, the processing unit is configured to receive as input initial positions of each of the one or more teeth and final positions of each of the one or more teeth, to determine a plurality of stages corresponding to a plurality of appliances to move the one or more teeth from the initial positions to the final positions, to determine the target position along a movement path of each of the one or more teeth for each stage and to determine the overcorrected position of each of the one or more teeth in response to the target position along the movement path for each stage.

In another aspect, a system for moving one or more teeth with a dental appliance is provided. The system can comprise a database comprising a plurality of correlations between teeth movements and force systems applied by dental appliances, and a processing unit coupled to the database. The processing unit can be configured to determine an initial position of the one or more teeth, determine a target position for each of the one or more teeth in a treatment plan, and determine a movement vector to move said each of the one or more teeth from the initial position to the target position with an overcorrected tooth receiving cavity position different from the target position in response to the plurality of correlations.

In many embodiments, the database comprises one or more of patient treatment histories, orthodontic therapies, orthodontic information, or diagnostics.

In many embodiments, the processing unit is configured to modify one or more tooth receiving cavity geometries of the dental appliance based on the overcorrected position.

In many embodiments, the movement vector is configured to establish a force system applied by the dental appliance to the tooth to move the tooth from the initial position to the overcorrected position. The force system, when applied by the dental appliance, may move the tooth from the initial position to a position closer to the target position than the overcorrected position. The force system can comprise one or more of a force, a moment of a force, or a moment of a couple.

In many embodiments, the movement vector is further determined in response to one or more of a minimum or maximum vertex distance.

In many embodiments, the processing unit is configured to receive as input initial positions of each of the one or more teeth and final positions of each of the one or more teeth, to determine a plurality of stages corresponding to a plurality of appliances to move the one or more teeth from the initial positions to the final positions, to determine the target position along a movement path of each of the one or more teeth for each stage and to determine the overcorrected position of each of the one or more teeth in response to the target position along the movement path for each stage.

In another aspect, a system for moving one or more teeth with a dental appliance is provided. The system can comprise a database comprising a plurality of clinical results of achieved teeth movements in response to force systems applied by dental appliances, and a processing unit coupled to the database. The processing unit can be configured to determine an initial position of the one or more teeth, determine a target position for each of the one or more teeth in a treatment plan, and determine a movement vector to move said each of the one or more teeth from the initial position to the target position with an overcorrected tooth receiving cavity position determined in response to the plurality of clinical results.

In many embodiments, the database comprises one or more of patient treatment histories, orthodontic therapies, orthodontic information, or diagnostics.

In many embodiments, the processing unit is configured to modify a tooth receiving cavity geometry of the dental appliance based on the overcorrected position.

In many embodiments, the movement vector is configured to establish a force system applied by the dental appliance to the tooth to move the tooth from the initial position to the overcorrected position. The force system, when applied by the dental appliance, may move the tooth from the initial position to a position closer to the target position than the overcorrected position. The force system can comprise one or more of a force, a moment of a force, or a moment of a couple.

In many embodiments, the movement vector is further determined in response to one or more of a minimum or a maximum vertex distance.

In many embodiments, the processing unit is configured to receive as input initial positions of each of the one or more teeth and final positions of each of the one or more teeth, to determine a plurality of stages corresponding to a plurality of appliances to move the one or more teeth from the initial positions to the final positions, to determine the target position along a movement path of each of the one or more teeth for each stage and to determine the overcorrected position of each of the one or more teeth in response to the target position along the movement path for each stage.

In another aspect, a method for determining one or more tooth receiving cavity positions of a dental appliance for moving one or more teeth is provided. The method can comprise: providing a database comprising prior treatment data corresponding to a plurality of discrepancies between target positions of teeth and achieved positions of teeth in response to treatments; determining an initial position of the one or more teeth; determining a target position of each of the one or more teeth in a treatment plan; and determining an overcorrected position of the one or more tooth receiving cavities in response the prior treatment data.

In many embodiments, the database comprises one or more of patient treatment histories, orthodontic therapies, orthodontic information, or diagnostics.

In many embodiments, the dental appliance is configured to apply a force system to the tooth to move the tooth from the initial position to the overcorrected position. The force system, when applied by the dental appliance, can move the tooth from the initial position to a position closer to the target position than the overcorrected position. The force system can comprise one or more of a force, a moment of a force, or a moment of a couple.

In many embodiments, determining the overcorrected position comprises limiting the overcorrected position in response to one or more of a minimum or maximum vertex distance.

In another aspect, a method for moving one or more teeth with a dental appliance is provided. The method can comprise: providing a database comprising a plurality of correlations between teeth movements and force systems applied by dental appliances; and determining one or more overcorrected positions of one or more tooth receiving cavities of the dental appliance in response to the plurality of correlations.

In many embodiments, the database comprises one or more of patient treatment histories, orthodontic therapies, orthodontic information, or diagnostics.

In many embodiments, the dental appliance is configured to apply a force system to the tooth to move the tooth from the initial position to the overcorrected position. The force system, when applied by the dental appliance, can move the tooth from the initial position to a position closer to the target position than the overcorrected position. The force system can comprise one or more of a force, a moment of a force, or a moment of a couple.

In many embodiments, determining the overcorrected position comprises limiting the overcorrected position in response to one or more of a minimum or maximum vertex distance.

In another aspect, a method for determining positions of one or more tooth receiving cavities of a dental appliance for moving one or more teeth is provided. The method can comprise: providing a database comprising a plurality of clinical results of achieved teeth movements in response to force systems applied by dental appliances; and determining an overcorrected position of the one or more tooth receiving cavities in response to the plurality of clinical results of achieved teeth movements in response to force systems applied by dental appliances.

In many embodiments, the database comprises one or more of patient treatment histories, orthodontic therapies, orthodontic information, or diagnostics.

In many embodiments, the dental appliance is configured to apply a force system to the tooth to move the tooth from the initial position to the overcorrected position. The force system, when applied by the dental appliance, can move the tooth from the initial position to a position closer to the target position than the overcorrected position. The force system can comprise one or more of a force, a moment of a force, and a moment of a couple.

In many embodiments, determining the overcorrected position comprises limiting the overcorrected position in response to one or more of a minimum or maximum vertex distance.

In another aspect, a method for moving teeth of a patient is provided. The method can comprise: providing a first appliance having a first plurality of overcorrected tooth-receiving cavities to move the teeth to first target positions, the first overcorrected tooth receiving cavities having positions different from the first target positions by first amounts; and providing a second appliance having a second plurality of overcorrected tooth-receiving cavities to move the teeth to second target positions, the second overcorrected tooth receiving cavities having positions different from the second target positions by second amounts; wherein the second amounts are less than the first amounts.

In many embodiments, the first amounts comprise a first plurality of first amounts and the second amounts comprise a second plurality of second amounts, each of the second plurality of second amounts less than a corresponding first amount of the first plurality of first amounts.

In many embodiments, the second overcorrections are provided after the first overcorrections. Alternatively, the second overcorrections can be provided before the first overcorrections.

In many embodiments, the method further comprises providing a third appliance having a third plurality of overcorrected tooth-receiving cavities to move the teeth to third target positions, the third overcorrected tooth receiving cavities having positions different from the third target positions by third amounts, wherein the third amounts are less than the first and second amounts. The third appliance can be provided before or after the second appliance.

In another aspect, a system for moving teeth of a patient is provided. The system can comprise: a first appliance having a first plurality of overcorrected tooth-receiving cavities to move the teeth to first target positions, the first overcorrected tooth receiving cavities having positions different from the first target positions by first amounts; and a second appliance having a second plurality of overcorrected tooth-receiving cavities to move the teeth to second target positions, the second overcorrected tooth receiving cavities having positions different from the second target positions by second amounts; wherein the second amounts are less than the first amounts.

In many embodiments, the first amounts comprise a first plurality of first amounts and the second amounts comprise a second plurality of second amounts, each of the second plurality of second amounts less than a corresponding first amount of the first plurality.

In many embodiments, the system further comprises a third appliance having a third plurality of overcorrected tooth-receiving cavities to move the teeth to third target positions, the third overcorrected tooth receiving cavities having positions different from the third target positions by third amounts, wherein the third amounts are less than the first and second amounts.

In another aspect, for a system or a method according to any of the embodiments herein, the one or more teeth comprise a plurality of teeth, and the appliance comprises a plurality of overcorrected teeth receiving cavities.

In another aspect, for a system or a method according to any of the embodiments herein, each overcorrected tooth receiving cavity comprises a three dimensional shape profile to receive a corresponding tooth having a corresponding three dimensional shape profile, the three dimensional shape profile of the tooth receiving cavity one or more of rotated or translated relative to the corresponding three dimensional shape profile of the corresponding tooth in the target position in order to define the overcorrected tooth receiving cavity position.

In another aspect, for a system or a method according to any of the embodiments herein, the overcorrected tooth receiving cavity comprises an over correction of a three dimensional shape profile along one or more of six degrees of freedom of the tooth receiving cavity of said each of the one or more teeth.

In another aspect, for a system or a method according to any of the embodiments herein, the appliance comprises a polymeric shell appliance and the polymeric shell appliance has been directly manufactured with one or more of 3D printing, stereo lithography, or fused deposition modeling.

In another aspect, a method for moving one or more teeth is provided comprising providing a system according to any of the embodiments herein.

In another aspect, a system or a method according to any of the embodiments herein further comprises instructions for manufacturing the dental appliance.

The methods, systems, and apparatus disclosed herein can be combined in many ways, and may comprise one or more components of known polymer shell appliances. Known shell appliances to reposition teeth may include features to facilitate the predictability of teeth movement. For example, such features may include "Active Attachment," "Activator," "Pressure Point," "Bite ramp," and "Power ridge" available in products of Align Technology, Inc. of Santa Clara, Calif. Such features may depend on adding features to the plain shell appliance and/or the teeth. For example, by active attachment with an activator or attachment, more torque can be created to rotate the canine or premolar. The power ridge may be used to create torque to move root in buccal-lingual direction. The polymer shell appliance inner surface may then be modified partially near the features attached or added to a tooth. However, the majority of the surface of the polymeric shell appliance may still be in the original position (i.e., the intended position of the teeth for the particular stage of treatment) and unchanged. The instant application refers to such a polymeric shell appliance as a "plain polymeric shell appliance."

As used herein, the terms "target position" and "planned position" are used interchangeably.

As used herein, the terms "patient" and "subject" are used interchangeably.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication as described herein, for example. Alternatively or in combination, the appliance can be fabricated with machining such as an appliance fabricated from a block of material with computer numeric control machining.

Examples of appliances such as polymeric shell appliances suitable for incorporation in accordance with embodiments of the present disclosure suitable are described in U.S. application Ser. No. 12/623,340, filed on Nov. 20, 2009, published as US 2010/0138025 on Jun. 3, 2010, entitled "Orthodontic systems and methods including parametric attachments", and U.S. application Ser. No. 13/865,091, filed on Apr. 17, 2013, published as US 2013/0230818, entitled "Method and system for optimizing dental aligner geometry", the entire disclosures of which are incorporated herein by reference.

In many instances and for many movements, a plain polymeric shell appliance may work well. Features can be added when there are difficult movements such as significant rotation, extrusion, or root movement. Even so, the plain polymeric shell appliance itself can still create the majority of force and moment to move the tooth.

A manufacturing process for a plain polymeric shell appliance may be as follows. First, initial and final teeth positions may be acquired and a movement path may be generated of all the teeth. Then, additional features such as attachments, dimples, and ridges may be added to the teeth. A 3D printer may then be used to print the physical mold of the teeth, jaw, and other features. A thin plastic sheet may be thermal formed on the mold. The gingival line may be cut and the polymeric shell appliance may be removed from the mold. Finally, the plain polymeric shell appliance may be cleaned and packaged.

In many embodiments, a processor comprises a user input and display for a user to position and orient a plurality of teeth at target positions and orientations for each stage of a treatment. Alternatively, the user may input position and orient the plurality of teeth at target final positions and orientations for the final stage of a treatment, and the processor may determine positions and orientations of the teeth at each of a plurality of intermediate stages of treatment. The processor may receive as input the plurality of initial positions and initial orientations of the teeth. The processor may comprise instructions to position teeth receiving cavities of the appliance at positions away from the target positions and orientations for each stage of a plurality of stages of the treatment in order to provide activation energy to the appliance. The processor may comprise instructions to output the positions of the teeth receiving cavities away from the target positions and orientations for each stage of the plurality of stages. The processor may comprise instructions to manufacture a plurality of appliances with indirect manufacturing comprising thermoforming or direct manufacturing comprising one or more of 3D printing, stereolithography, or fused deposition modeling, for example. In many embodiments, the processor generates instructions for fabricating one or more appliances and transmits the instructions to a fabrication machine, e.g., configured to fabricate the appliances using indirect manufacturing or direct manufacturing, or combinations thereof.

The plain polymeric shell appliance can be made from the tooth position from the initial and final positions. In software, for example, the tooth position can be designed with the following principles in mind. The teeth may not collide with each other in all stages, or else the course of treatment can include removal of parts of one or more teeth. Additionally, in some embodiments, teeth are not moved too fast because of biological limitations.

Accordingly, the tooth movement path generated for each stage of treatment can be related to the limit that the tooth can be moved for the particular stage of treatment. The polymeric shell appliance itself, however, can be used to move the tooth but not to limit tooth movement, for example. The force from a polymeric shell appliance can be created because the appliance can be based on the teeth positioning of the next stage of treatment and put on the full dentition of the patient in the current stage of treatment.

In this present disclosure, improved methods of creating polymeric shell appliances are provided. Instead of creating a polymeric shell appliance with teeth receiving cavities corresponding to the position of a tooth in the next stage of treatment, the appliance can be created based on a modified, overcorrected tooth position, for example. In this modified tooth position, force and moment may be created to move the tooth root in the desired direction, rather than limiting the tooth to next position. A schematic of a modified tooth position for targeting the tooth root is shown in FIG. 1.

FIG. 1 shows a schematic of a tooth in various positions—a current position 102 (e.g., current position 102a), a desired target position 104 comprising the planned location of the tooth at the end of the treatment stage (e.g., next planned position 104a), an actual resulting position 106 from the application of a plain polymeric shell appliance (e.g., an achieved position with no overcorrection 106a, which may exhibit lag in the translation and/or tipping relative to the next planned position 104a), an overcorrected position 112 (e.g., overcorrected position 112a, which may exhibit more translation to create more force and/or rotation to compensate for tipping and to move the root relative to the next planned position 104a), and an actual resulting position 114 from the application of a polymeric shell appliance of the present disclosure configured to overcorrect as described herein (e.g., achieved position with overcorrection 114a, which may be close to or substantially match the next planned position 104a). Because the force and moment generated can decrease as the appliance and tooth discrepancy decreases, there can be a discrepancy between the desired target position 104 and the actual position 106 that is achieved. There may be a lag in the translation of the tooth as indicated by the arrow 108. There may be tipping or rotation from the root as indicated by the arrow 110. According to embodiments of the present disclosure, a polymeric shell appliance may be configured with the tooth receiving cavities of the appliance at locations corresponding to an overcorrected position 112. More translation may be provided versus the uncorrected appliance to create more force. Rotation may be added to compensate for the tipping effect and move the root. The force and moment generated can decrease as the discrepancy between appliance and tooth decreases. A discrepancy can remain, however, between the overcorrected position 112 of the tooth receiving cavity and the actual position 114 that is achieved, as the tooth moves toward the target position. The resulting position 114 from the overcorrection can more closely match the desired target position 104 in the course of treatment.

The appliances such as polymeric shell appliances can be configured in one or more of many ways with the overcorrected tooth receiving cavities to move one or more teeth as described herein. The tooth comprises a tooth profile, such as a three dimensional shape profile, and the tooth receiving cavity of the polymeric shell appliance may comprise a corresponding internal three dimensional shape profile to receive the tooth. The position of the shape profile of the tooth receiving cavity of the polymeric shell appliance can be overcorrected in relation to the next planned position of the tooth. Alternatively or in combination, the orientation of the three dimensional shape profile of the tooth receiving cavity can be overcorrected in relation to the next planned orientation of the tooth.

The overcorrection with the three dimensional shape profile of the tooth receiving cavity can be provided along one or more of six degrees of freedom. The overcorrection can be provided along two or more degrees of freedom, for example along one translational and one rotational degree of freedom. The overcorrection can be provided along three or more degrees of freedom, for example along two translational and one rotational degree of freedom. The amount of overcorrection along each degree of freedom can be determined in response to clinical data, for example. Additional degrees of freedom of the tooth receiving cavities can be overcorrected to move the tooth to the planned position and orientation.

The appliance can be configured to move a plurality of teeth with a plurality of overcorrected tooth receiving cavities at each of a plurality of stages of the treatment as described herein. Each of the plurality of overcorrected tooth receiving cavities can be configured to move the corresponding tooth of the plurality of teeth to the planned target position.

Figure 2:
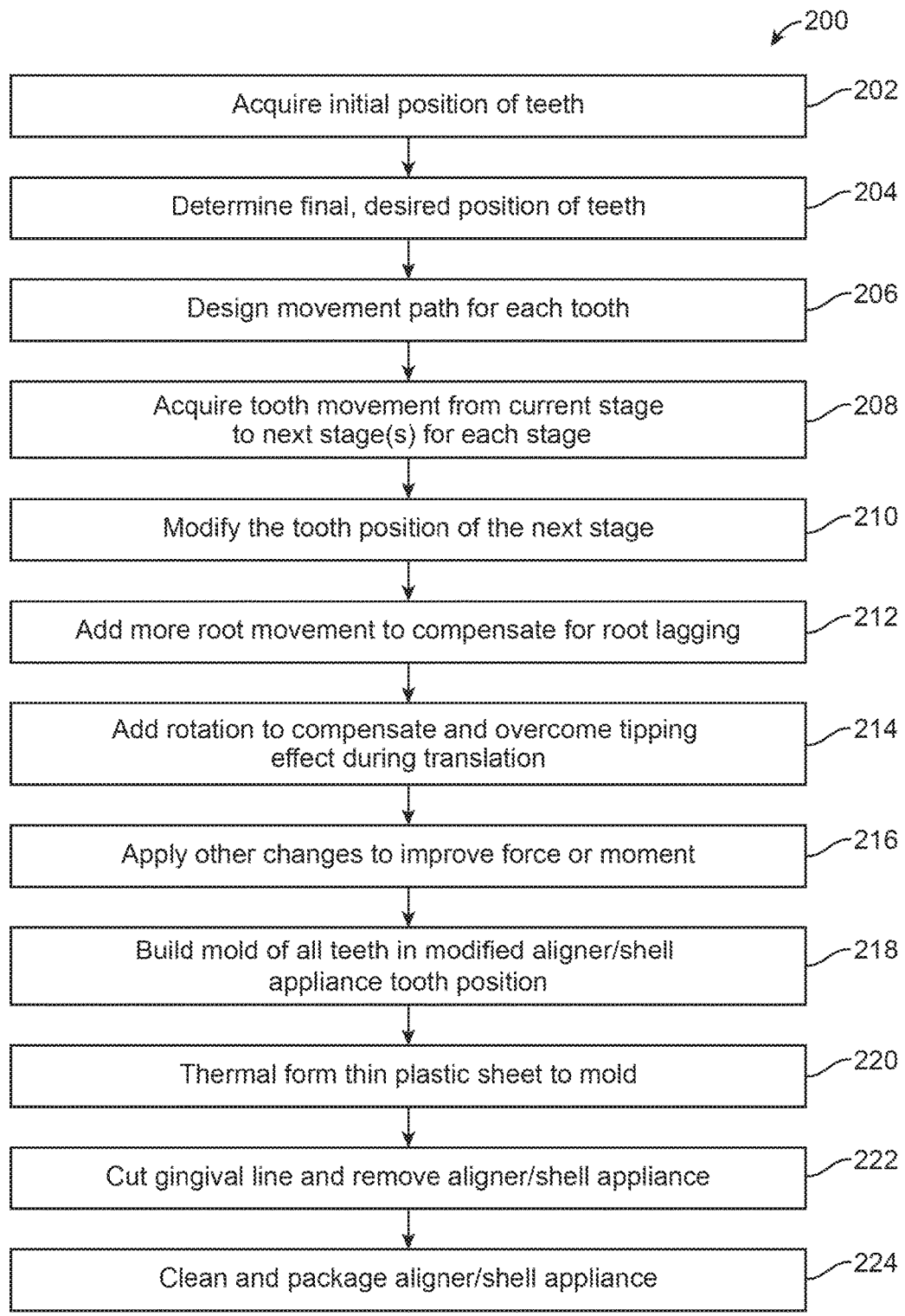
FIG. 2 shows a flowchart of a method of manufacturing a set of polymeric shell appliances with overcorrection, according to many embodiments.

Referring to FIG. 2, an exemplary method 200 of creating a polymeric shell appliance may be as follows. In a step 202, the initial position of the teeth of a subject may be acquired and input to a processor. In a step 204, the final, desired position of the teeth of the subject at the end of a course of treatment may be determined and input to a processor. In a step 206, the movement path for each tooth may be designed. The movement path may be designed such that, at each stage of treatment, the teeth may not collide with each other and may move at a limited speed (e.g., 0.25 mm/treatment stage, which may for example be 2 weeks). In a step 208, the tooth movement from the current stage to next stage or next several stages may be acquired. In a step 210, the tooth position of next stage may be modified so sufficient force is created (i.e., the discrepancy from the current to next stage is sufficiently large) to move the tooth closely to the desired target position. The modification of step 210 can be performed with an overcorrection in one or more of many ways. For example, the tooth position may be overcorrected as described herein. In a step 212, more root movement may be added to compensate for the tooth root lagging during the movement, for example with overcorrection of one or more of the position or orientation of the tooth receiving cavity. In a step 214, rotation may be added to compensate and overcome the tipping effect while tooth is in bodily translation (e.g., for space closure treatment), for example with overcorrection of one or more of the position or orientation of the tooth receiving cavity. In a step 216, other changes may be applied to improve the force or moment applied, for example with overcorrection of one or more of the position or orientation of the tooth receiving cavity. In a step 218, a mold of all teeth in the modified aligner (i.e., overcorrected polymeric shell appliance) tooth position and jaw may be created. Other features such as like attachment and power ridges may be added. The mold may be created using 3D printing technology, for example. In a step 220, a thin plastic sheet may be thermal formed to the mold to create the aligner or appliance. In a step 222, the gingival line may be cut from the molded sheet and the aligner or appliance may be removed from the mold. In a step 224, the aligner or appliance may be cleaned and packaged. Alternatively or in combination, the appliance can be fabricated directly, for example with one or more of 3D printing, stereo lithography, or fused deposition modeling of the appliance, for example.

Although the above steps show the method 200 of generating a set of polymeric shell appliances overcorrected to move teeth in an improved manner in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

One or more of the steps of the method 200 may be performed with circuitry as described herein, for example one or more of a processor or logic circuitry of a computer or a computerized system. The circuitry may be programmed to provide one or more of the steps of the method 200, and the program may comprise program instructions stored on a computer readable memory or programmed steps of the logic circuitry, for example.

Aspects of the present disclosure provide several ways to modify the tooth position for the aligner or polymeric shell appliances, which are discussed herein and as follows. The methods of modifying the tooth position may be applied alone, in various combinations, or in various combinations of their component steps or parts.

1. Modify Tooth Position Based on Achievement Statistics

The appropriate overcorrection may be determined using achievement statistics. Achievement statistics describe the relationship between the achieved and planned tooth movement for post treatment (or in the middle treatment) cases. A tooth can be considered as a rigid body and its movement can be described by 6 degrees of freedom (DOFs), or 3 translation and 3 rotations. Optionally, the achievement statistics provide data corresponding to discrepancies between achieved and planned target positions of teeth in response to treatment.

After the treatment, the teeth are moved to a new position close to the planned final position, but not exactly the same. The movement from the initial tooth position to this new position may be called the achieved movement. The achieved movement can be measured by taking a new impression, and comparing it to the initial impression. Alternatively or in combination, other types of data besides impressions can be used, such as scans or images of the teeth.

The relationship between the planned movement and the achieved movement can be described by a statistical relationship called a Planned-Achievement Relation.

The achievement statistics can show coupling among planned movements and achieved movements, and cross-coupling among terms can be used to design the polymeric shell appliance.

The Planned-Achievement Relation can be estimated by data analysis of a large number of treated cases. In some embodiments, linear regression may be used.

The Planned-Achievement Relation estimated from the after treatment cases can represent full movement, i.e., from an initial position of the teeth to the final position of the teeth. The Planned-Achievement Relation for a single stage (which may be referred to as a stage Planned-Achievement Relation) can be computed from the full Planned-Achievement Relation when the stage number is known. The overcorrection can be computed from the Planned-Achievement Relation. From the Planned-Achievement Relation, it can be known that the desired final positions of the teeth may not be fully achieved using a plain aligner or polymeric shell appliance. An overcorrection may be used to amplify and correct the movement.

However, the overcorrection movement can be adjusted more to deal with complicated tooth movement. A consideration may be to blend the overcorrection with planned movement. In some embodiments, when treatment is started, the overcorrection should not be too great because a greater than necessary overcorrection may apply too great a force to the root and cause the patient pain and/or discomfort. After several weeks, teeth may start moving and the bone near the root may get soft because of the biological response. Then, further overcorrection can be added. In some embodiments, when the treatment is reaching the final stage, the overcorrection can be reduced to let the tooth move closer to the final position, rather than having a larger overcorrection position.

The data from clinical studies can be fit, for example, with a linear regression of the coefficients of the achievement matrix and $R^2$ values determined.

Figure 3:
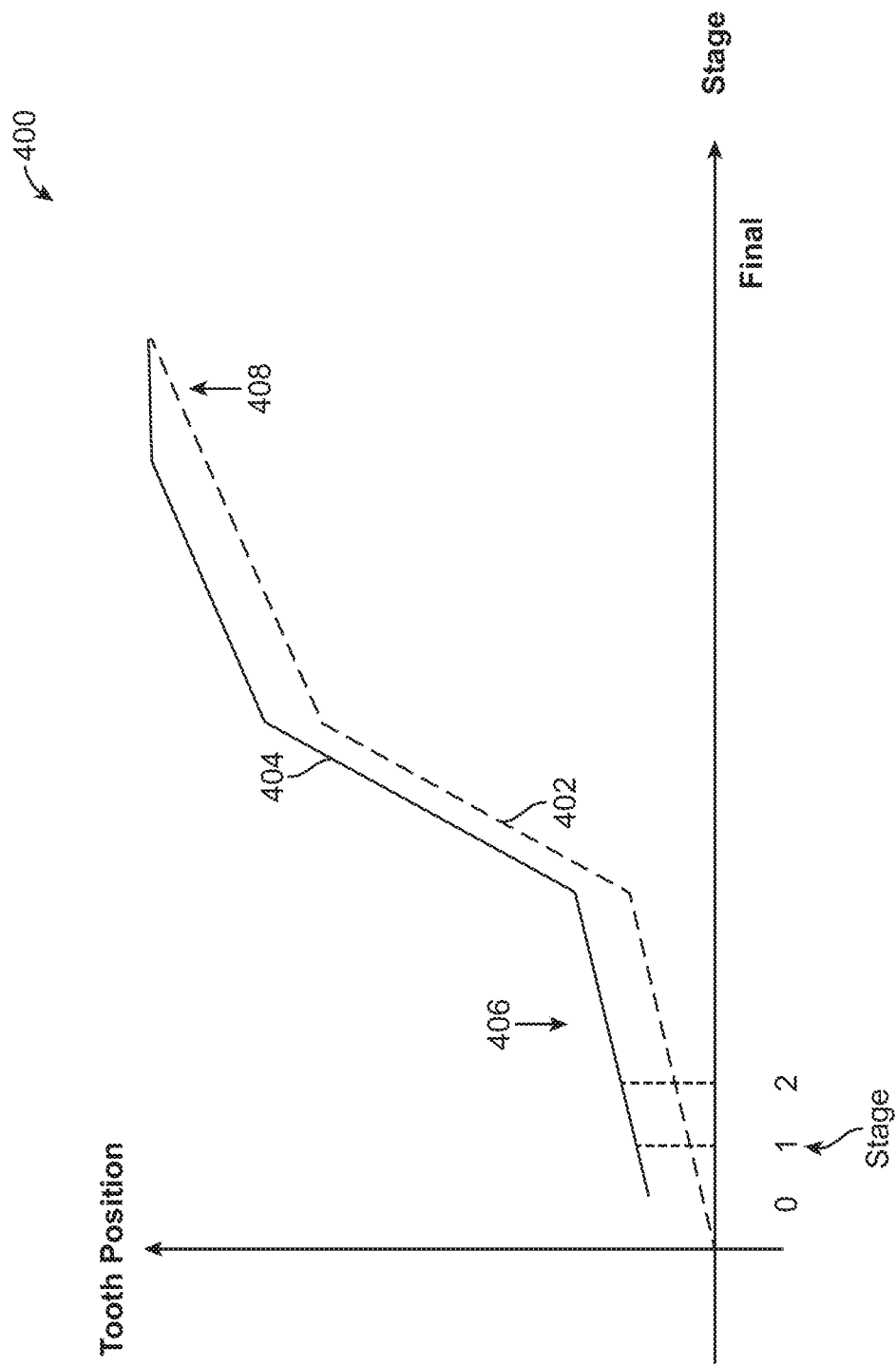
FIG. 3 shows a graph of the discrepancy between a planned tooth path and an overcorrected tooth path, according to many embodiments.

The change of overcorrection is shown in the overcorrection graph 400 of FIG. 3. The graph 400 shows the planned tooth path 402 of one or more teeth of the subject, and the overcorrected tooth receiving cavity path 404 for a plurality of stages of treatment, e.g., 0 (initial prior to treatment), 1, 2, etc. to N, where N is the final stage. The graph 400 includes a line for the planned tooth path 402, which can be compared to the overcorrected tooth path 404. There may be greater overcorrection at early stage 406 versus at the later stage 408. Each stage has a planned tooth position of the subject and a corresponding overcorrected tooth position of the tooth receiving cavity of the appliance as shown with the dashed line of stages 1 and 2, for example. Each of the plurality of teeth receiving cavities of an appliance for a stage can be overcorrected with reference to the tooth position as described herein. The tooth receiving cavities of the final stage may or may not be overcorrected, and the appliance may be left on the teeth for a longer amount of time to ensure that the teeth have moved to the final target positions.

The processing unit as described herein can be configured with instructions to receive as input initial positions of each of the one or more teeth and final positions of each of the one or more teeth. The processing unit can be configured with instructions to determine a plurality of stages corresponding to a plurality of appliances to move the one or more teeth from the initial positions to the final positions. The processing unit can be configured to determine the target position along a planned movement path of each of the one or more teeth for each stage and to determine the overcorrected position of each of the one or more tooth receiving cavities in response to the target position along the movement path for each stage, for example.

The overcorrection may be gradually reduced to none as the treatment course nears completion. Such reduction in the overcorrection may be provided to allow the soft tissue of the patient to begin to set, for example.

Improved methods and systems to move teeth by applying such gradually decreasing overcorrections are provided by the present disclosure. The positions of the tooth receiving cavities of the appliance can be located to provide overcorrection force vectors to the teeth. For example, if the target location of the tooth for the present stage is located 0.2 mm from the position of the immediately prior stage, the tooth receiving cavity can be located 0.3 mm from the position of the prior stage in order to provide overcorrection with the desired force vector, for example. A first overcorrected force vector may be applied on teeth to move the teeth to a first target position with a first overcorrected tooth receiving cavity of a first appliance. The first overcorrected force vector may have a first overcorrection directed to move the teeth to a first overcorrected position different from the first target position. A second overcorrected force vector may then be applied on the teeth to move the teeth to a second target position with a second overcorrected tooth receiving cavity of a second appliance. The second overcorrected force vector may have a second overcorrection directed to move the teeth to a second overcorrected position different from the second target position. The second overcorrection may be less than the first overcorrection and may be applied after the first overcorrection. A third overcorrected force vector may be applied on the teeth to move the teeth to a third target position with a third over corrected tooth receiving cavity of a third appliance. The third overcorrected force vector may have a third overcorrection directed to move the teeth to a third overcorrected position different from the third target position. The third overcorrection may be less than the first and second overcorrections. First, second, and/or third shell appliances having first, second, and/or third pluralities of tooth-receiving cavities, for example, may be provided and configured to apply the first, second, and/or third overcorrected force vectors on the tooth, for example. A person of ordinary skill in the art will recognize variations in one or more of the order, timing or amount of overcorrection.

Another adjustment may include the minimum and maximum crown movement. In some embodiments, to move the tooth, enough force but not too large of a force should be applied to the tooth. For an aligner or polymeric shell appliance, the force created can be related to the discrepancy between the aligner or appliance to the tooth. The overcorrection movement can be modified as follows and as described herein.

The maximum movement distance for all crown surface points, from the current position to the overcorrection position, can be measured. This maximum vertex distance can be bigger than one number, for example, 0.2 mm. This distance can be less than another number, for example 0.50 mm. If the distance is too big or small, the overcorrection movement can be increased or reduced by multiplying the movement vector.

Figure 4:
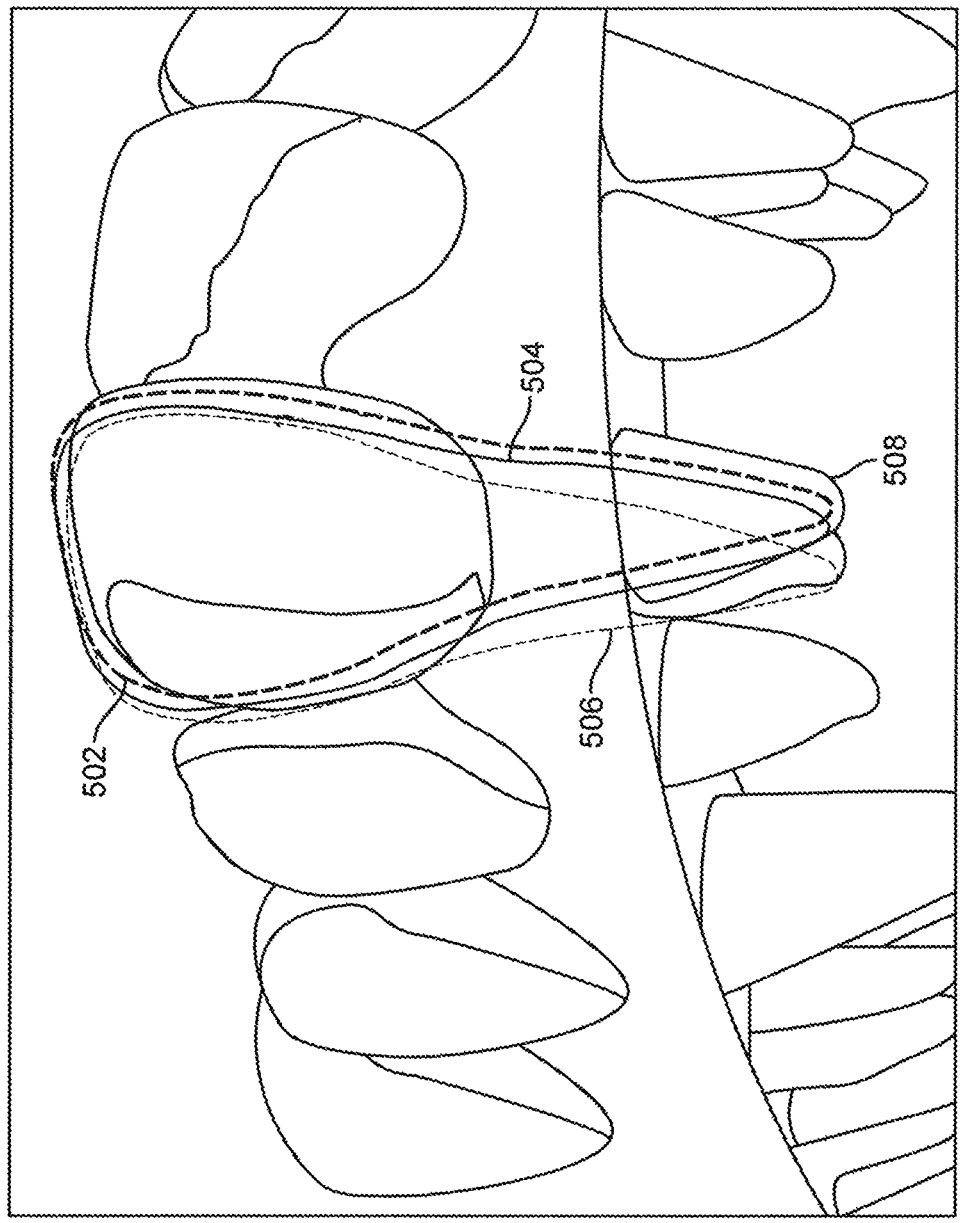
FIG. 4 shows a schematic of a tooth in a current position, a next planned position, and an overcorrected position, according to many embodiments.

FIG. 4 shows a schematic of tooth positions and is an example of a tooth in a current position 502, a planned target position 504, and an overcorrected target position 506. It can be seen that the overcorrected target position 506 can involve more movement than the planned target position 504, particularly for root part 508. The greater movement may be because the root can be normally hard to move so the aligner or polymeric shell appliance can be manufactured to move root 508 more.

Figure 5:
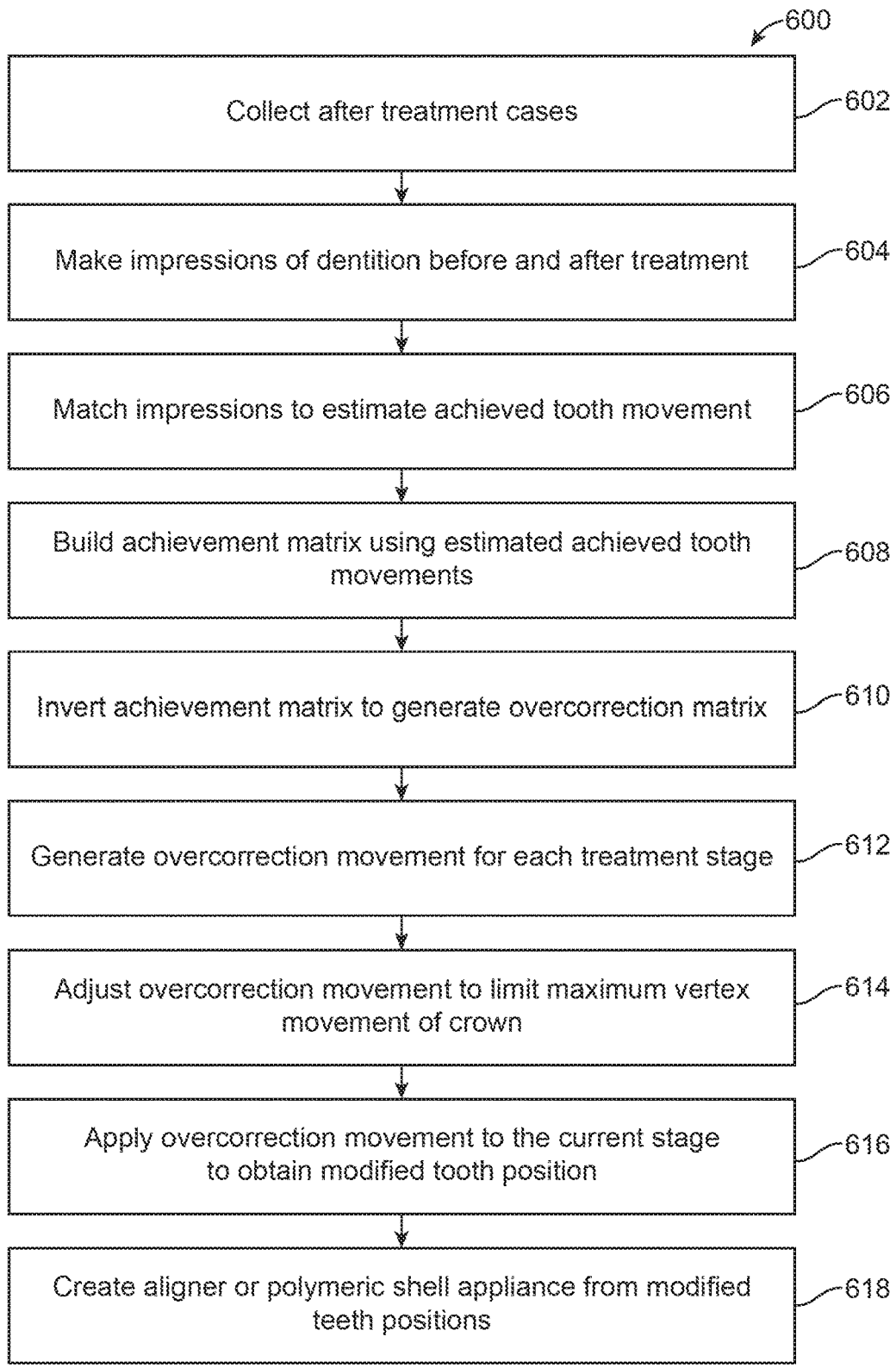
FIG. 5 shows a flowchart of a method of manufacturing a set of polymeric shell appliances with overcorrection, according to many embodiments.

FIG. 5 shows a flow chart of a method 600 of creating a polymeric shell appliance using an "achievement matrix" as described herein and above. In a step 602, after treatment cases for various patients may be collected. In a step 604, impressions of the dentition of the various patients may be made before and after the treatment to estimate the tooth movement achieved. In a step 606, the impressions may be matched to estimate the achieved tooth movement. Alternatively or in combination, other types of data besides impressions can be used, such as scans or images of the dentition before and after treatment. In a step 608, an achievement matrix may be built using the estimated achieved tooth movements of the various embodiments. The achievement matrix may be built using data analysis such as linear regression. In a step 610, the achievement matrix may be inverted to generate the overcorrection matrix. The achievement matrix can be used to correct tooth movement in response to one or more discrepancies. In a step 612, the overcorrection movement for each treatment stage may be generated by acquiring the plan movement vector for each treatment stage and multiplying by the overcorrection matrix. In a step 614, the overcorrection movement may be adjusted so the maximum vertex movement of the crown is not too small or too large (e.g., greater than 0.2 mm and less than 0.5 mm). In a step 616, the overcorrection movement may be applied to the current treatment stage to obtain the modified tooth position. In a step 618, an aligner or polymeric shell appliance may be created from the modified tooth positions of all teeth.

Although the above steps show the method 600 of generating a set of polymeric shell appliances overcorrected to move teeth in an improved manner in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

One or more of the steps of the method 600 may be performed with circuitry as described herein, for example one or more of a processor or logic circuitry of a computer or a computerized system. The circuitry may be programmed to provide one or more of the steps of the method 600, and the program may comprise program instructions stored on a computer readable memory or programmed steps of the logic circuitry, for example.

2. Modify Tooth Position Based on Clinical and/or Mechanical Knowledge.

Another method of generating the overcorrections may be to use clinical and/or mechanical knowledge based on a history of multiple cases of treatment to move teeth with aligners or polymeric shell appliances. The clinical and/or mechanical knowledge can provide information regarding correlations between teeth movements and force systems applied by dental appliances, as well as clinical results of achieved teeth movements in response to force systems applied by dental appliances.

For example, when using aligners or polymeric shell appliances to treat a premolar extraction case, there may be an undesirable tipping effect of the canine when the space is closed. When the canine is translated distally, force can be mostly applied to the crown, which can tip the canine toward the molar. After the treatment is finished, the canine root may be straight and not aligned well with the other teeth. To better straighten and align the canine root, an attachment may be provided to the canine to add more torque and compensate for the tipping. Alternatively or in combination, the tooth position may be modified with some rotation or torque.

Figure 6:
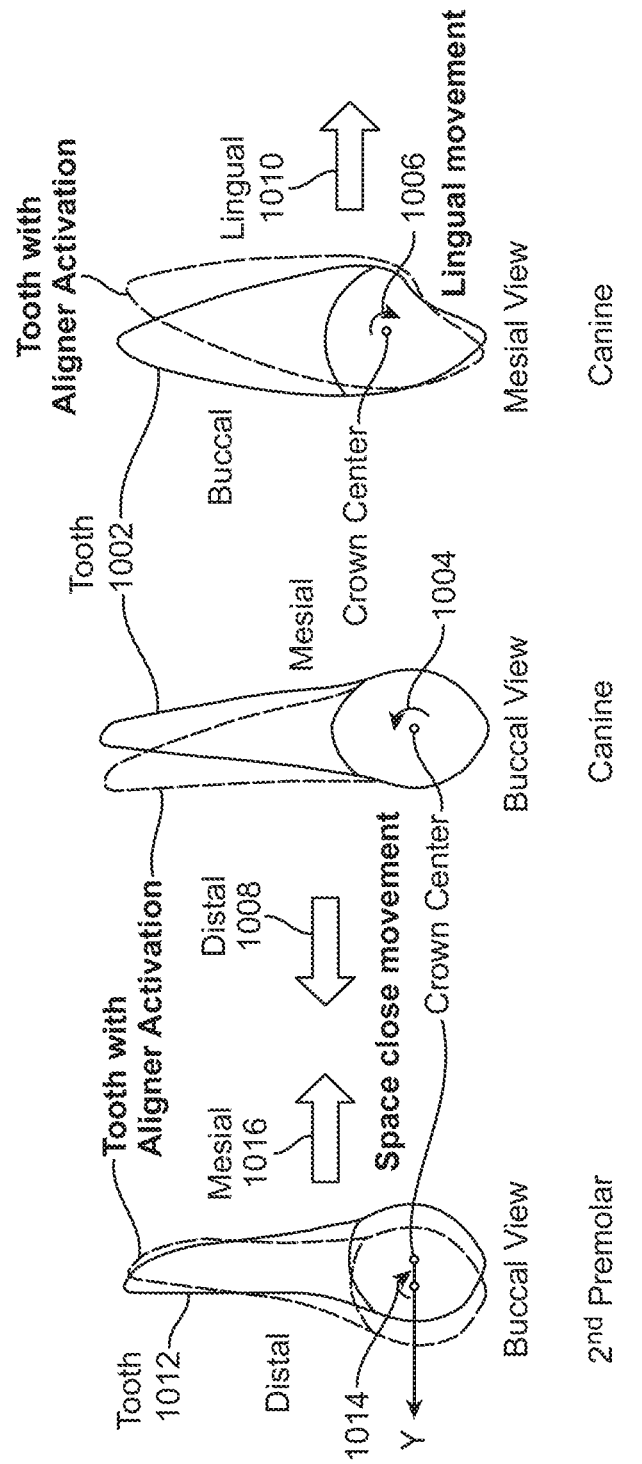
FIG. 6 shows a schematic of rotational tooth movement generated by a polymeric shell appliance, according to many embodiments.

Referring to FIG. 6, to create such a modified position, one may first determine whether premolar extraction or space closure treatment is appropriate. For canines 1002, the root apex may be rotated distally (around the X axis of the crown basis) as indicated by the arrow 1004 and lingually (around the Y axis of the crown basis) as indicated by the arrow 1006. The tipping from the distal translation as indicated by arrow 1008 and lingual movement as indicated by arrow 1010 can thereby be compensated. For the activation of a second premolar 1012, the root apex can be rotated mesially (around the X axis of the crown basis) as indicated by the arrow 1014 and the second premolar can be translated distally as indicated by the arrow 1016 in the meantime.

Figure 7:
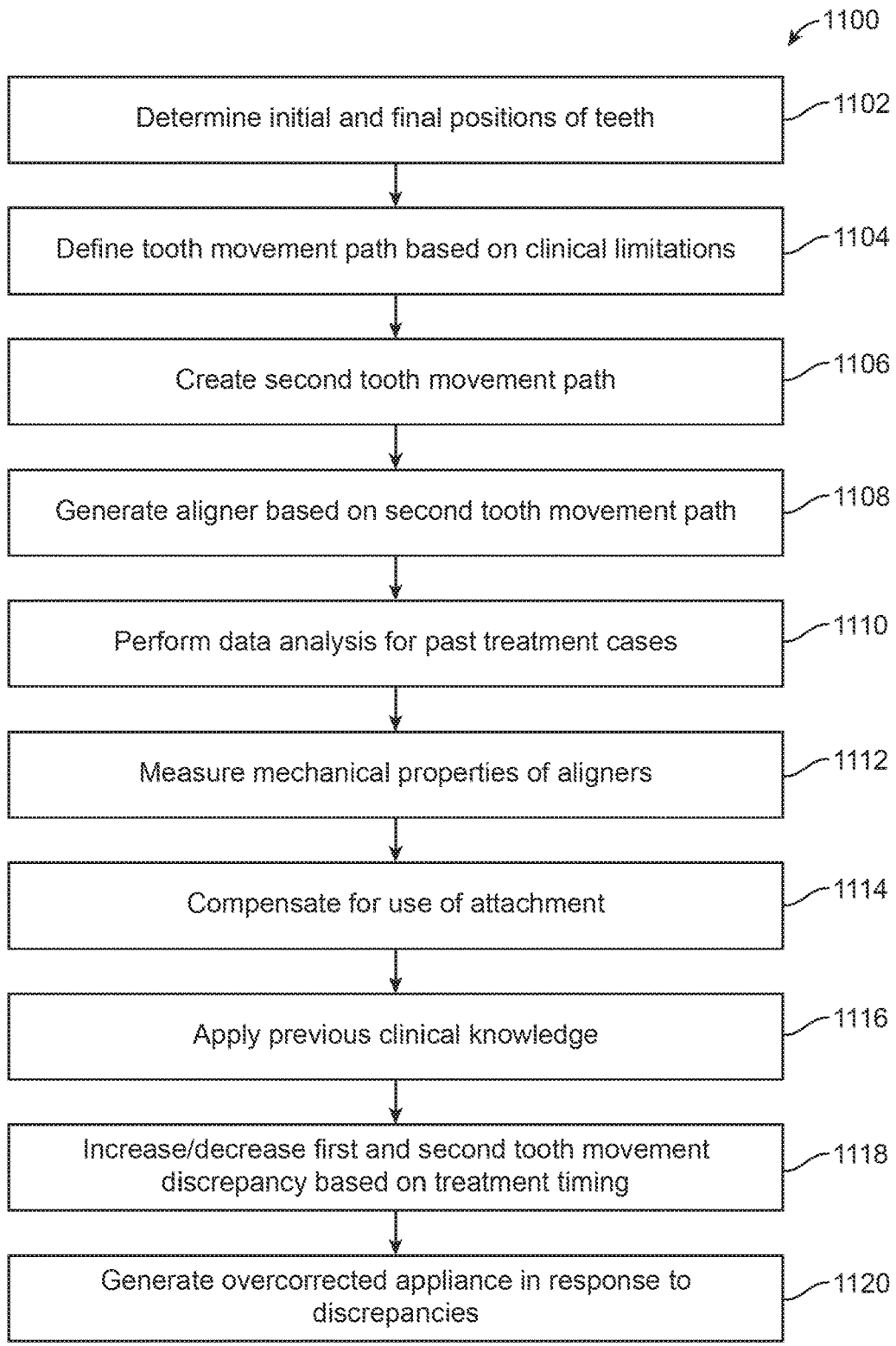
FIG. 7 shows a flowchart of a method of manufacturing a set of polymeric shell appliances with overcorrection, according to many embodiments.

Referring to FIG. 7, a method 1100 of generating an overcorrected polymeric shell appliance can be as follows. First, the initial and final positions of teeth in the course of treatment may be determined in a step 1102. Then, the tooth movement path may be defined based on clinical limitations in a step 1104, for example, to avoid the tooth collision and velocity (0.25 mm/2 weeks). From the first tooth movement path, a second tooth movement path may be created in a step 1106 and used to generate an aligner or polymeric shell appliance in a step 1108. The limitation(s) of the tooth arrangement in the second path can be bigger than that of the first path. For example, tooth collision may be allowed, and the velocity can be bigger than 0.25 mm for 2 weeks.

The knowledge to generate the second tooth movement path or arrangement can be drawn from various sources. In a step 1110, for example, data analysis may be performed for past treatment cases. In a step 1112, for example, the mechanical properties (i.e., the force/torque created) of various aligners or polymeric shell appliances may be measured in a laboratory. In a step 1114, for example, the overcorrection may account for attachments to the teeth such as a power ridge and the like. If an attachment is used, the overcorrection can be small because attachment may already help engagement and create force. In a step 1116, for example, previous clinical knowledge may be applied. In a step 1118, the overcorrection or modification from the first to second tooth paths may be larger for the initial and middle stages of the treatment, while getting smaller when the treatment is close to completed so that the final tooth arrangement is close to the final position.

In a step 1120, an overcorrected appliance is generated in response to one or more discrepancies as described above.

Although the above steps show the method 1100 of generating a set of polymeric shell appliances overcorrected to move teeth in an improved manner in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

One or more of the steps of the method 1100 may be performed with circuitry as described herein, for example one or more of a processor or logic circuitry of a computer or a computerized system. The circuitry may be programmed to provide one or more of the steps of the method 1100, and the program may comprise program instructions stored on a computer readable memory or programmed steps of the logic circuitry, for example.

Figure 8A:
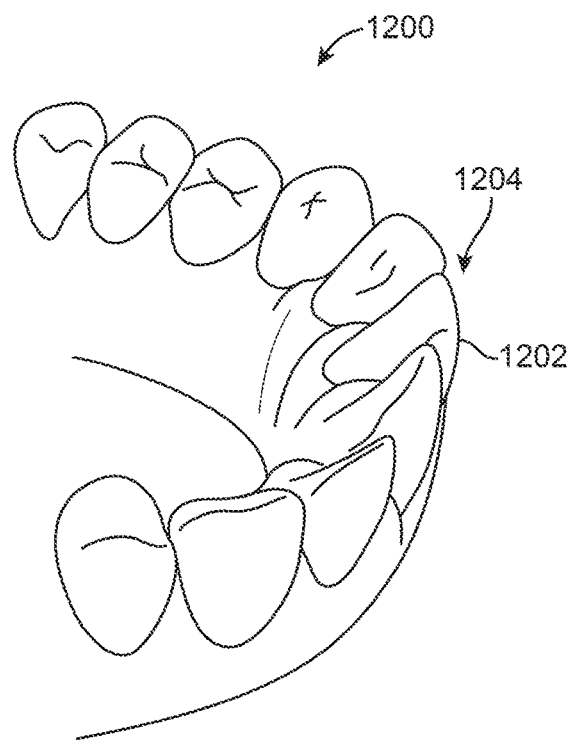
FIG. 8A shows a three-dimensional model of a patient's teeth in a target position, according to many embodiments.

FIG. 8a shows and embodiment of a three-dimensional model 1200 of a target position of a patient's teeth, in particular a lower arch. The target position may be a final target position that represents a desired final position of the patient's teeth after treatment or a target intermediate position of the patient's teeth at the end of a step or stage of treatment. The three-dimensional model 1200 is created based on a model of the initial position of the patient's teeth and a dental practitioner's prescription for a target position of the teeth.

A method for producing the incremental position adjustment appliances for subsequent use by a patient to reposition the patient's teeth will be described. As a first step, a digital data set representing an initial tooth arrangement is obtained. The digital data set may be obtained in a variety of ways. For example, the patient's teeth may be scanned or imaged using well known technology, such as X-rays, three-dimensional X-rays, computer-aided tomographic images or data sets, and magnetic resonance images. Methods for digitizing such conventional images to produce useful data sets are well known. Usually, however, the teeth of the patient are scanned a plaster cast of the patient's teeth is obtained by well known techniques and then plaster cast is then scanned of the patient's teeth are scanned directly using know techniques.

When the initial data set is obtained from a tooth casting, the casting is digitally scanned by a scanner, such as a non-contact type laser, a destructive scanner, or a contact-type scanner, to produce the initial data set. The data set produced by the scanner may be presented in any of a variety of digital formats to ensure compatibility with the software used to manipulate images represented by the data, as described in more detail below.

Suitable scanners include a variety of range acquisition systems, generally categorized by whether the acquisition process requires contact with the three dimensional object being scanned. Some contact-type scanners use probes having multiple degrees of translational and/or rotational freedom. A computer-readable (i.e., digital) representation of the sample object is generated by recording the physical displacement of the probe as it is drawn across the sample surface.

Conventional non-contact-type scanners include reflective-type and transmissive-type systems. A wide variety of reflective systems are in use today, some of which utilize non-optical incident energy sources such as microwave radar or sonar. Others utilize optical energy. Non-contact-type systems that use reflected optical energy usually include special instrumentation that carry out certain measuring techniques (e.g., imaging radar, triangulation and interferometry).

One type of non-contact scanner is an optical, reflective scanner, such as a laser scanner. Non-contact scanners such as this are inherently nondestructive (i.e., do not damage the sample object), generally are characterized by a relatively high capture resolution, and are capable of scanning a sample in a relatively short period of time.

Both non-contact-type and contact-type scanners also can include color cameras which, when synchronized with the scanning capabilities, provide means for capturing, in digital format, color representations of the sample objects.

Other scanners, such as destructive scanners produced can also provide detailed and precise information about a patient's teeth. In particular, a destructive scanner can image areas that are hidden or shielded from a range acquisition scanner and therefore may not be subject to adequate imaging. A destructive scanner gathers image data for an object by repeatedly milling thin slices from the object and optically scanning the sequence of milled surfaces to create a sequence of 2D image slices, so none of the object's surfaces are hidden from the scanner. Image processing software combines the data from individual slices to form a data set representing the object, which later is converted into a digital representation of the surfaces of the object, as described below.

The destructive scanner may be used in conjunction with a laser scanner to create a digital model of a patient's teeth. For example, a laser scanner may be used first to build a low resolution image of a patient's upper and lower arches coupled with the patient's wax bite. The destructive scanner then may be used to form high-resolution images of the individual arches. The data obtained by the laser scanner indicates the relation between the patient's upper and lower teeth which later can be used to relate to each other the images generated by the destructive scanner and the digital models derived from them.

The destructive scanner can be used to form the digital data set of the patient's teeth by milling and scanning a physical model, such as a plaster casting, of the teeth. To ensure a consistent orientation of the casting throughout the destructive scanning process, a scanning system operator pots the casting in potting material and cures the material in a pressure vacuum (PV) chamber to form a mold. The color of the potting material is selected to contrast sharply with the color of the casting material to ensure the clarity of the scanned image.

A slicing mechanism mills a thin slice from the mold, and then the optical scanner scans the surface to create a 2D image data set representing the surface. This milling and scanning process is repeated until the entire mold is scanned. The resulting output of the destructive scanning system is a 3D image data set.

A 3D surface model of the patient's teeth is then created from the data set using know techniques. Once a 3D model of the tooth surfaces has been constructed, models of the patient's individual teeth can be derived. In one approach, individual teeth and other components are segmented to permit individual repositioning or removal of teeth in or from the digital data. The teeth in the model may be segmented either manually or automatically, as known in the art.

After the tooth components are segmented, a prescription or other written specification provided by the treating professional is followed to reposition the teeth. Alternatively, the teeth may be repositioned based on the visual appearance or based on rules and algorithms programmed into the computer. Once an acceptable final arrangement has been created, the final tooth arrangement is incorporated into a final target data set.

Based on both the initial data set and the final target data set, a plurality of intermediate data sets are generated to correspond to successive intermediate tooth arrangements. The system of incremental position adjustment appliances can then be fabricated based on the intermediate data sets, as described in more detail below.

The system can be configured to add roots and hidden surfaces to the tooth models to allow more thorough and accurate simulation of tooth movement during treatment. In alternative implementations, this information is added automatically without human assistance, semi-automatically with human assistance, or manually by human operator, using a variety of data sources.

In some embodiments, 2D and 3D imaging systems, such as x-ray systems, computed tomography (CT) scanners, and MRI systems, are used to gather information about the roots of the patient's teeth. For example, several 2D x-ray images of a tooth taken in different planes allow the construction of a 3D model of the tooth's roots. Information about the roots is available by visual inspection of the x-ray image and by application of a computer-implemented feature identification algorithm to the x-ray data. The system adds the roots to the tooth model by creating a surface mesh representing the roots. Physical landmarks on the patient's teeth, e.g., cavities or cusps, are extracted from the 2D and 3D data and are used to register the roots to the tooth model. Like the roots, these landmarks can be extracted manually or by use of a feature detection algorithm.

Another alternative for the addition of roots and hidden surfaces is to model typical root and crown shapes and to modify the digital model of each tooth to include a root or a hidden surface corresponding to a typical shape. This approach assumes that the roots and hidden surfaces of each patient's teeth have typical shapes. A geometric model of each typical shape is acquired, e.g., by accessing an electronic database of typical root and crown models created before the analysis of a particular patient's teeth begins. Portions of the typical root and crown models are added to the individual tooth models as needed to complete the individual tooth models.

Yet another alternative for the addition of roots and hidden surfaces is the extrapolation of the 3D tooth model to include these features based on observed characteristics of the tooth surfaces. For example, the system can use the curvature of a particular molar between the tips of the cusps and the gumline to predict the shape of the roots for that molar. In other implementations, x-ray and CT scan data of a patient's teeth are used to provide comparison points for extrapolation of the patient's roots and hidden surfaces. Models of typical root and crown shapes also can be used to provide comparison points for root and hidden surface extrapolation.

After the teeth have been placed or removed to produce a model of the final tooth arrangement, a treatment plan is generated. The treatment plan includes the series of intermediate tooth position data sets. To produce these data sets, the movement of selected individual teeth are defined or mapped from the initial position to the final position over a series of successive steps. In addition, other features may be added to the data sets in order to produce desired features in the treatment appliances. For example, it may be desirable to add wax patches to the image in order to define cavities or recesses for particular purposes, such as to maintain a space between the appliance and particular regions of the teeth or jaw in order to reduce soreness of the gums, avoid periodontal problems, allow for a cap, and the like. Additionally, a practitioner may wish to provide a receptacle or aperture intended to accommodate an anchor which is to be placed on a tooth in order to permit the tooth to be manipulated in a manner that requires the anchor, e.g., to be lifted relative to the jaw.

After the treatment plan is created or the final target position of the patient's teeth is determined, a three-dimensional model of the patient's teeth in a target position may be displayed. A three-dimensional GUI is advantageous for both component manipulation and for display to both the patient and dental practitioner.

Such an interface provides the treating professional or user with instant and visual interaction with the digital model components. Before or during the manipulation process, one or more tooth components may be augmented with template models of tooth roots. The component manipulation software is designed to operate at a sophistication commensurate with the operator's training level. For example, the component manipulation software can assist a dental practitioner by automatically overcorrecting a final target position of a patient's tooth for use in generating an appliance such that the final target position is more likely to be achieved.

In some embodiments, the final target potions of the patient's teeth, also referred to as a clinical goal, are displayed to the dental practitioner, for example, as shown in FIG. 8a, which shows a digital model 1200 of a patient's lower arch and with a patient's tooth 1202 in a target position 1204. A dental practitioner experienced in the field of teeth repositioning with aligners may manipulate the target position of the patient's teeth based on their own experience with aligners, in order to apply their own overcorrection. Such manual overcorrection, when combined with the overcorrection applied based on one or more of the methods discussed above, may result in the patient's teeth reaching an undesired final position at the final stage of treatment. In some embodiments, the system may generate instructions for generating or displaying the three-dimensional model of the patient's teeth in an initial position.

Figure 8B:
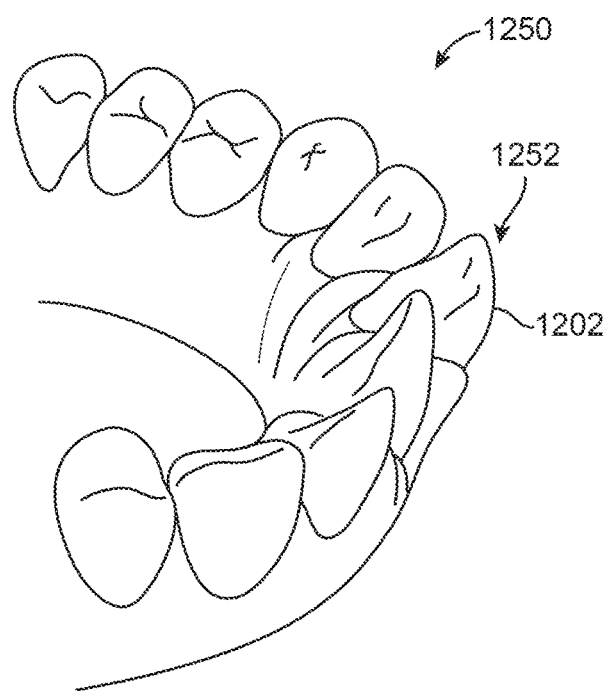
FIG. 8B shows a three-dimensional model of a patient's teeth in an overcorrected position, according to many embodiments.

To help guide the dental practitioner in developing a target position of a patient's teeth, the three-dimensional GUI may also display a three-dimensional model of the overcorrected position of the patient's teeth. For example, FIG. 8b shows a three-dimensional model 1250 of the lower arch of a patient's teeth that includes the tooth 1202 in a final overcorrected position 1252. In this way, a dental practitioner is made aware of both the target position of the patient's teeth and the overcorrected position of the patient's used in manufacturing the aligners. In some embodiments, the system may generate instructions for generating or displaying the three-dimensional model of the patient's teeth in a target position.

In some embodiments, a doctor may manipulate teeth in one or both of the target position model 1200 and the overcorrected model 1250. In such embodiments, a change made in one of the models may be reflected in the other model. For example, a dental practitioner may adjust the target position 1204 of the patient's tooth 1202. This adjustment may result in changes to the overcorrected position 1252 of the patient's tooth 1202 in the overcorrected model 1250. Therefore, in some embodiments, the overcorrected model 1250 may be updated to reflect the changes such changes. In some embodiments, such changes occur in real-time or near real-time, such as during the same viewing session. In some embodiments, the system may generate revised instructions for generating or displaying the three-dimensional model of the patient's teeth in an overcorrected or overengineered position.

As another example, a practitioner may instead desire to adjust the position 1252 of the tooth 1202 in the overcorrected model. In such an embodiment, the target position 1204 of the tooth 1202 in the target model 1200 may change to reflect a new target position that is based on the new overcorrected position. In other embodiments, a practitioner may make adjustments or refinements to the position 1252 of the tooth 1202 in the overcorrected model 1250, but not have such changes reflected in the target model. For example, the practitioner's adjustments may be made to the overcorrected model 1250 based on the practitioner's experience with aligners in a particular situation and based on that experience, the practitioner provides instructions for a different overcorrected position in order to reach the same target position.

Figure 9:
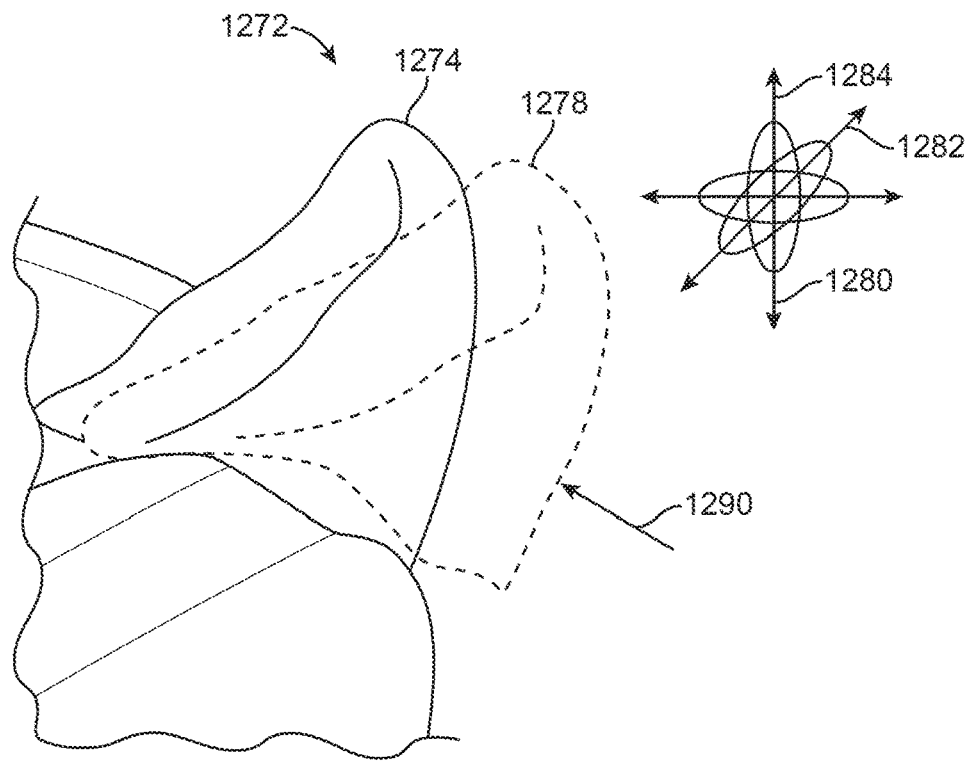
FIG. 9 shows a three-dimensional model of a patient's teeth and a digital tool, according to many embodiments.

FIG. 9 shows an example of the six degrees of freedom about which a tooth's position may be moved. In some embodiments, a practitioner may use one or more digital tools 1290 to manipulate the target position 1274 or the overcorrected position 1278 of the tooth 1272. For example, as shown in FIG. 9 the tooth position may be displaced along the facial-distal axis 1280, the mesial-distal axis 1282, or the incisal-root axis 1284 and may also be rotation around one or more of the axis 1280, 1282, 1284.

Figure 10:
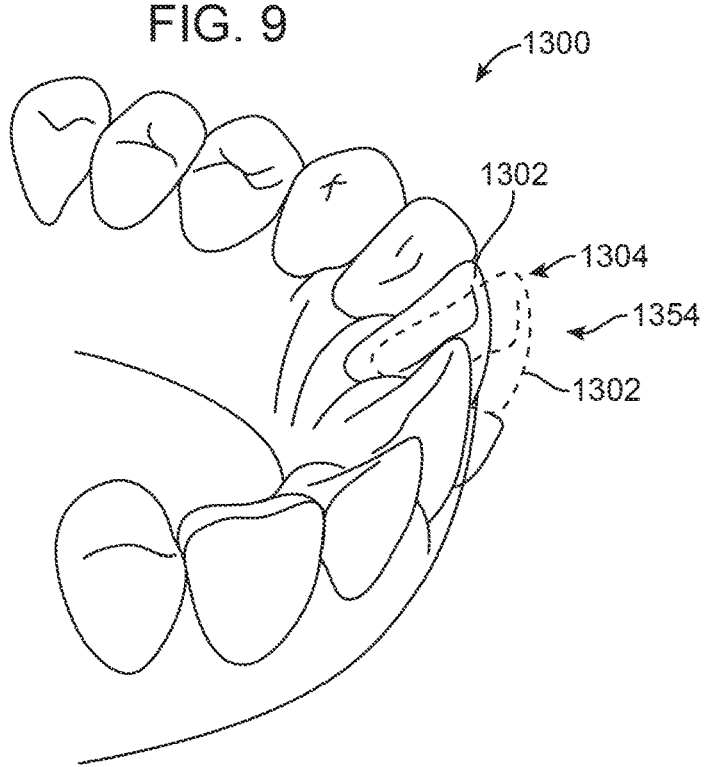
FIG. 10 shows a three-dimensional model of a patient's teeth in a target position with a three-dimensional model of a patient's teeth in an overcorrected position, according to many embodiments.

In some embodiments, rather than or in addition to displaying the target position and overcorrected position as separate, spaced apart digital models, the target position model and the overcorrected model may be overlaid or superimposed over one another. For example, FIG. 10 shows a target model 1300 of a patient's tooth 1302 in a target position 1304 and also shows the overcorrected position 1354 of the patient's tooth 1302.

Figure 11:
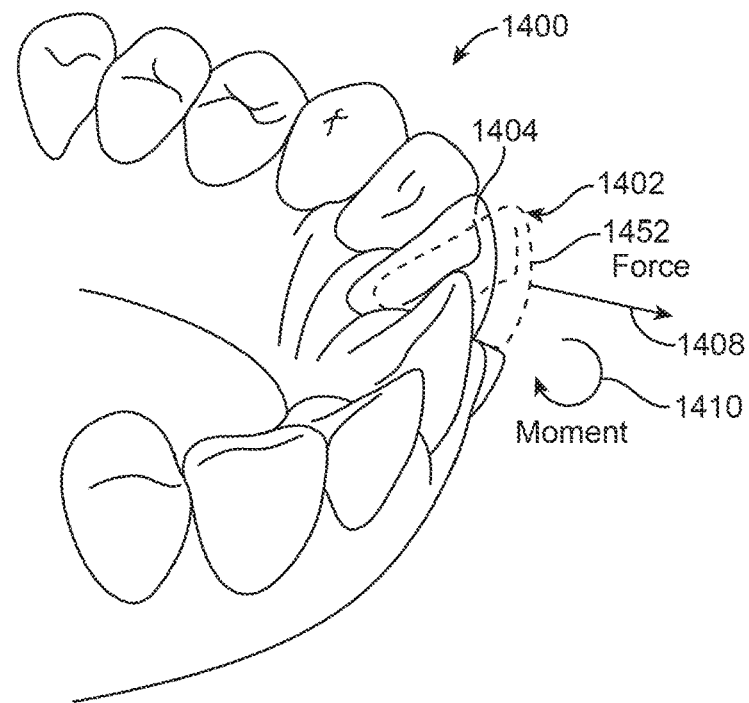
FIG. 11 shows a three-dimensional model of a patient's teeth in a target position with a three-dimensional model of a patient's teeth in an overcorrected position and a force system, according to many embodiments.

In some embodiments, the force and moment created by the deformation of the polymeric shell appliance while it is on the teeth may be shown along with the target position model, the overcorrected position model, or both models. For example, FIG. 11 shows an embodiment of a target model 1400 of a patient's tooth 1402 in a target position 1404 along with the overcorrected position 1454 of the patient's tooth 1402 and also depicts the force 1408 and moment 1410 applied to the tooth 1402 based on the overcorrected position 1452 of the tooth 1402. The force and moment caused by the deformation of polymeric shell appliance can be computed by mathematical model or simulation, including, for example, VILab simulation or finite element analysis (FEA) of the shell deformation. The force and moment can also be measured via mechanical test of the aligner on a mold of a patient's teeth, or for example, an FMA test. The visualization of the force 1408 and moment 1410 aides the practitioner in determining the appropriate overcorrection for reaching the desired target position.

Figure 12:
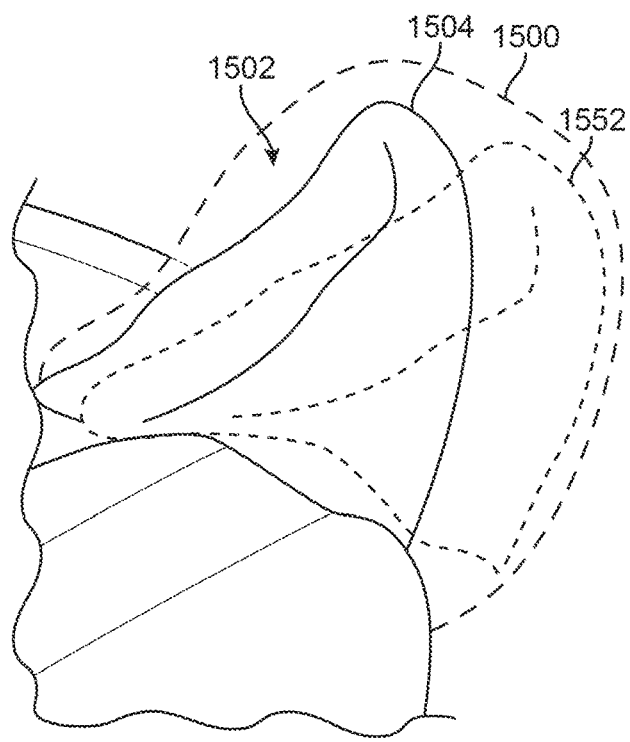
FIG. 12 shows a three-dimensional model of a patient's teeth in a target position with a three-dimensional model of a patient's teeth in an overcorrected position and a volume, according to many embodiments.

Referring now to FIG. 12, a visualization of a volume 1500 around a target position 1504 of a tooth 1502 may define a limited zone around the tooth 1502 is shown. In some embodiments, for example, the target volume may indicate to the practitioner one or more of a manufacturing zone, a safety zone, a treatment threshold, an aligner fit threshold, and a prediction of the off-track position of a tooth. One such zone is a safety zone. A safety zone is the maximum discrepancy (e.g., displacement) of one or more feature points on the tooth between the feature's location when the tooth is in a target position and when the tooth is in an overcorrected position. For example, the discrepancy of a crown center on a tooth should be less than 1 mm. As another example, the rotation around Z-axis should be less than, for example 10 degrees. Another example is an aligner fit threshold, which can be tested and verified using mechanical experiments like FMA. For example, in an FMA test of an aligner fit threshold, if the extrusion is set to a large quantity, such as 1 mm, and an attachment on a tooth does not engage to a shell, then no extrusion force is created and the aligner fit threshold should be 1 mm or less. As another example, a prediction of off-track position is a zone representing possible final positions of the tooth and may be considered a tolerance around the prediction for the treatment.

Although the visualizations discussed above have been described with reference to target and overcorrected final and intermediate positions of a patient's teeth, such visualizations of models of a patient's teeth may also be applied in embodiments of tooth movements including staged movements of patient's teeth and in aligner shape modifications.

Figure 13:
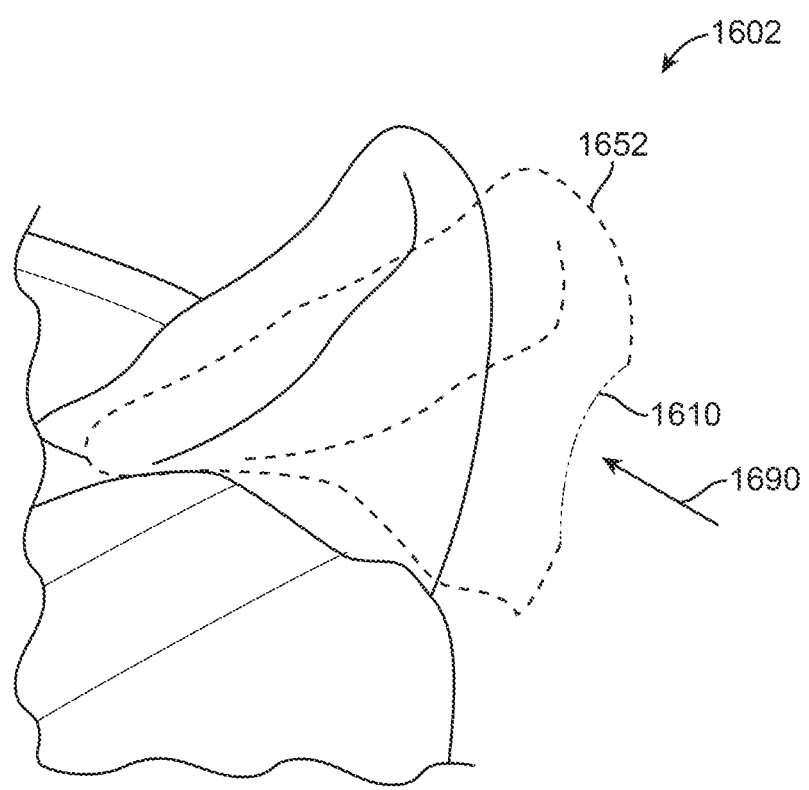
FIG. 13 shows a three-dimensional model of a patient's teeth and a digital tool, according to many embodiments.

For example, referring now to FIG. 13, an embodiment of an aligner shape modification is shown. The overcorrected position 1652 of the tooth 1602 is shown with a modification 1610 to the surface of the tooth using a digital tool 1690. Such modifications 1610 may include a cavity facing dimple, as shown in FIG. 13, or other shapes such as a linear dimple (ridge), a large cavity covering most of a tooth surface (pressure area), or a localized offset alleviating contact between aligner and tooth (bubble). When the aligner is formed based on the overcorrected position 1652 and modifications 1610 to the shape of the tooth the aligner may apply a set of forces and moments to the tooth 1602. Such forces and moments may also be depicted, for example as explained with reference to FIG. 11.

Figure 14:
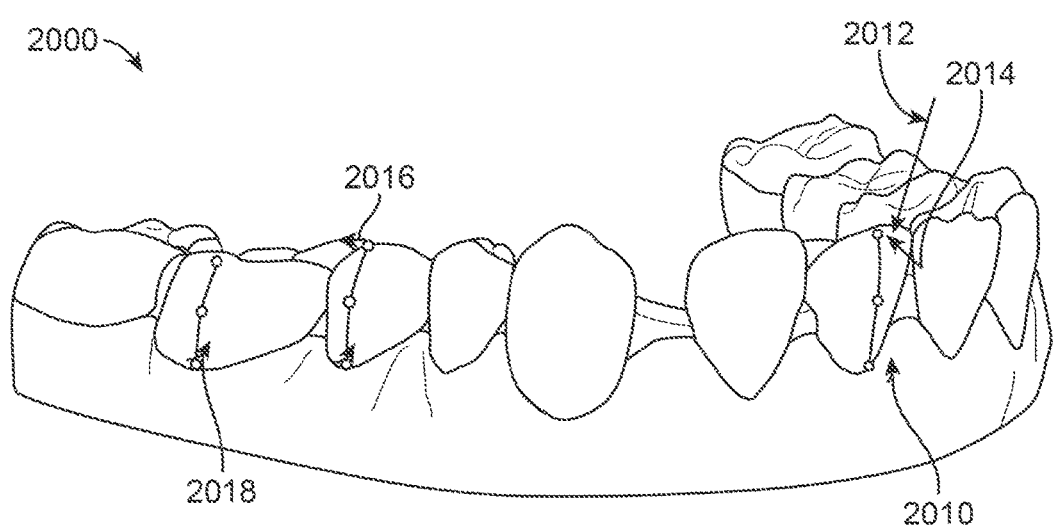
FIG. 14 shows a three-dimensional model of a patient's teeth.

In some embodiments, the displacements of the tooth receiving cavities as compared to the tooth positions may be shown along. For example, FIG. 14 shows an embodiment of a model 2000 of a patient's teeth in a position along with indicators of the translation and rotation displacements of the tooth receiving cavity as compared to the tooth position the patient's tooth. The translation indicators 2012, 2014, 2014 show the relative magnitude and direction of the displacement of a tooth receiving cavity as compared to the position of the tooth at a stage of treatment in three axis, such as the orthogonal x,y,z translation, x,y,z rotation axis of three dimensional Cartesian coordinate systems. The indicators may also show translation and rotations according to a tooth or oral axis, for example, indicator 2012 indicates translation in the extrusion-intrusion direction, indicator 2014 indicates translation in the buccal-lingual direction, and arrow 2016 shows side-to-side translation along the arch of the teeth. Rotational indicators 2010, 2018 show rotational movement about respective axis, for example, indicator 2018 shows rotation about the buccal-lingual axis while 2010 shows rotation about the side-to-side arch directional axis. Rotational indicators may also indicate rotation about the extrusion-intrusion axis. The visualization of the translation and rotation aides the practitioner in determining the appropriate overcorrection for reaching the desired target position.

The depiction of overengineering of the position and shape of a patient's tooth, including overcorrection, staging, shape, etc, may be applicable to all phases of treatment of a patient's tooth. For example, the visualizations may be used during development of the initial treatment plan, during progress tracking, during adaptive treatment planning, during the development of additional aligners, and other stages of treatment.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for determining one or more tooth receiving cavity positions of a dental appliance for moving one or more teeth, the system comprising:
   a database comprising data corresponding to one or more of: (1) a plurality of discrepancies between target positions of teeth and achieved positions of the teeth in response to treatment, (2) a plurality of correlations between teeth movements and force systems applied by dental appliances, or (3) a plurality of clinical results of achieved teeth movements in response to force systems applied by dental appliances;
   a processing unit coupled to the database, wherein the processing unit is configured to:
      determine a target position for each of the one or more teeth in a treatment plan;
      determine an overcorrected tooth receiving cavity position and tooth position determined in response to the data in the database;
      generate a three-dimensional model of the patient's tooth in an overcorrected position and a three-dimensional model of the patient's tooth in the target position;
      display the three-dimensional model of the patient's tooth in an overcorrected position and a three-dimensional model of the patient's tooth in the target position;
      receive one of an adjusted target tooth position or an adjusted overcorrected tooth position;
      generate an updated three-dimensional model of the patient's tooth in a second overcorrected position and an updated three-dimensional model of the patient's tooth in a second target position based on the received adjustment; and
      display the updated three-dimensional model of the patient's tooth in the second overcorrected position and the updated three-dimensional model of the patient's tooth in the second target position based on the received adjustment.

2. The system of claim 1, wherein the processing unit is configured to receive instructions for a modified overcorrected tooth position.

3. The system of claim 1, wherein the processing unit is configured to generate instructions for displaying the three-dimensional model of the patient's tooth in the target position.

4. The system of claim 3, wherein the processing unit is configured to generate instructions for displaying, at the same time, the three-dimensional model of the patient's tooth in the target position and the overcorrected position.

5. The system of claim 1, wherein the three-dimensional model of the patient's tooth in the target position and the overcorrected position includes the overcorrected position of the tooth overlaid over the target position of the tooth.

6. The system of claim 1, wherein the processing unit is configured to determine a movement vector to move said each of the one or more teeth from an initial position to the target position with an overcorrected tooth receiving cavity position determined in response to the data in the database.

7. The system of claim 6, wherein the processing unit is configured to establish a force system applied by the dental appliance to each tooth to move the tooth in the direction of the movement vector, from the initial position to the target position, with the overcorrected tooth receiving cavity position.

8. The system of claim 7, wherein the processing unit is configured to generate instructions for displaying the force system applied by the dental appliance to at least one tooth.

9. The system of claim 8, wherein the force system comprises one or more of a force, a moment of a force, or a moment of a couple.

10. The system of claim 1, wherein the processing unit is configured to generate instructions for displaying a visualization volume about the three-dimensional model of the patient's tooth.

11. The system of claim 1, wherein the processing unit is configured to receive instructions for a modified tooth shape.

12. The system of claim 11, wherein the processing unit is configured to generate instructions for fabricating the dental appliance.

13. The system of claim 1, wherein the processing unit is configured to generate instructions for fabricating the dental appliance.

14. A method for determining one or more tooth receiving cavity positions of a dental appliance for moving one or more teeth, the method comprising:
providing a database comprising data corresponding to one or more of: (1) a plurality of discrepancies between target positions of teeth and achieved positions of teeth in response to treatments, (2) a plurality of correlations between teeth movements and force systems applied by dental appliances, or (3) a plurality of clinical results of achieved teeth movements in response to force systems applied by dental appliances;
determining a target position of each of the one or more teeth in a treatment plan;
determining an overcorrected position of one or more tooth receiving cavities of the dental appliance and overcorrected tooth positions in response to the data in the database;
determining an overcorrected position of the one or more teeth in response to the data in the database; and
generating a three-dimensional model of one or more of the patient's teeth in an overcorrected position and a three-dimensional model of the patient's tooth in the target position;
displaying the three-dimensional model of the patient's tooth in an overcorrected position and a three-dimensional model of the patient's tooth in the target position;
receiving one of an adjusted target tooth position or an adjusted overcorrected tooth position;
generating an updated three-dimensional model of the patient's tooth in a second overcorrected position and an updated three-dimensional model of the patient's tooth in a second target position based on the received adjustment; and
displaying the updated three-dimensional model of the patient's tooth in the second overcorrected position and the updated three-dimensional model of the patient's tooth in the second target position based on the received adjustment.

15. The method of claim 14, further comprising:
receiving instructions for a modified overcorrected tooth position.

16. The method of claim 14, further comprising:
generating instructions for displaying the three-dimensional model of the patient's tooth in the target position.

17. The method of claim 16, further comprising:
generating instructions for displaying, at the same time, the three-dimensional model of the patient's tooth in the target position and the overcorrected position.

18. The method of claim 14, further comprising:
generating instructions for displaying the three-dimensional model of the patient's tooth in the target position; and
generating instructions for displaying the three-dimensional model of the patient's tooth in the overcorrected position overlaid over the three-dimensional model of the patient's tooth in the target position.

19. The method of claim 14, further comprising:
determining a movement vector to move each of the one or more teeth from the initial position to the target position with an overcorrected tooth receiving cavity position determined in response to the data in the database.

20. The method of claim 19, further comprising:
determining a force system applied by the dental appliance to each tooth to move the tooth in the direction of the movement vector, from the initial position to the target position, with the overcorrected tooth receiving cavity position.

21. The method of claim 20, further comprising:
generating instructions for displaying the force system applied by the dental appliance to at least one tooth.

22. The method of claim 21, wherein the force system comprises one or more of a force, a moment of a force, or a moment of a couple.

23. The method of claim 14, further comprising:
generating instructions for displaying a visualization volume about the three-dimensional model of the patient's tooth.

24. The method of claim 14, further comprising:
receiving instructions for a modified tooth shape.

* * * * *